United States Patent
Herr et al.

(10) Patent No.: US 7,313,463 B2
(45) Date of Patent: Dec. 25, 2007

(54) BIOMIMETIC MOTION AND BALANCE CONTROLLERS FOR USE IN PROSTHETICS, ORTHOTICS AND ROBOTICS

(75) Inventors: Hugh M. Herr, Somerville, MA (US); Andreas G. Hofmann, Cambridge, MA (US); Marko B. Popovic, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/499,853

(22) Filed: Aug. 4, 2006

(65) Prior Publication Data

US 2007/0016329 A1  Jan. 18, 2007

Related U.S. Application Data

(63) Continuation-in-part of application No. 11/395,448, filed on Mar. 31, 2006.
(60) Provisional application No. 60/705,651, filed on Aug. 4, 2005, provisional application No. 60/704,517, filed on Aug. 1, 2005, provisional application No. 60/666,876, filed on Mar. 31, 2005.

(51) Int. Cl.
*G06F 19/00* (2006.01)
(52) U.S. Cl. ......................... 700/245; 700/246; 700/251; 700/253; 700/260; 700/261; 318/568.1; 318/568.12; 318/568.16; 318/568.17; 318/568.2; 901/1; 901/9; 901/46
(58) Field of Classification Search ................. 700/245, 700/246, 251, 253, 260, 261; 318/568.1, 318/568.12, 568.16, 568, 17, 568.2; 901/1, 901/9, 46
See application file for complete search history.

(56) References Cited

U.S. PATENT DOCUMENTS

| | | | | |
|---|---|---|---|---|
| 5,294,873 A | * | 3/1994 | Seraji ....................... | 318/568.1 |
| 6,144,385 A | * | 11/2000 | Girard ....................... | 345/424 |
| 7,136,722 B2 | * | 11/2006 | Nakamura et al. .......... | 700/245 |
| 7,145,305 B2 | * | 12/2006 | Takenaka et al. ....... | 318/568.12 |

OTHER PUBLICATIONS

Sarrigeorgidis et al., Motion control of the N.T. U. A. robotic snake on a planar surface, 1998, IEEE, p. 2977-2981.*
Yun, Dynamic state feedback control of constrained robot manipulators, 1988, IEEE, p. 622-626.*

* cited by examiner

*Primary Examiner*—Thomas Black
*Assistant Examiner*—McDieunel Marc
(74) *Attorney, Agent, or Firm*—Charles G. Call

(57) ABSTRACT

Systems for controlling the motion of multiple articulated elements connected by one or more joints in an artificial appendage system. Four different embodiments includes a controller that reduces the dimension of joint state space by utilizing biomechanically inspired motion primitives; a quadratic proportional-derivative (PD) controller which employs a two-stage linearization method, applies constraints to variables for dynamic stability, and employs a corrective "sliding control" mechanism to account for errors in the linear model used; a non-prioritized balance control approach that employs enforced linear dynamics in which all control variables are truncated to linear terms in joint jerks; and a biomimetic motion and balance controller based on center of mass (CM) energetic and biomimetic zero moment conditions.

21 Claims, 12 Drawing Sheets

A)

B)

BIOMIMETIC MOTION AND BALANCE CONTROLLERS FOR USE IN PROSTHETICS, ORTHOTICS AND ROBOTICS

CROSS REFERENCE TO RELATED APPLICATIONS

This application is a non-provisional of, and claims the benefit of the filing date of, U.S. Provisional Patent Application Ser. No. 60/705,651 filed on Aug. 4, 2005, the disclosure of which is incorporated herein by reference.

This application is a continuation in part of, and claims the benefit of the filing date of, U.S. patent application Ser. No. 11/395,448 filed on Mar. 31, 2006, which was a non-provisional of U.S. Provisional Patent Applications Ser. No. 60/666,876 filed on Mar. 31, 2005 and Ser. No. 60/704,517 filed on Aug. 1, 2005, the disclosure of which is incorporated herein by reference.

FIELD OF THE INVENTION

This invention relates generally to prosthetic devices and artificial limb systems, including robotic, orthotic, exoskeletal limbs, and more particularly to motion and balance control systems for use with such systems.

BACKGROUND OF THE INVENTION

In the course of the following description, reference will be made to the papers, patents and publications presented in a list of references at the conclusion of this specification. When cited, each listed reference will be identified by a numeral within curly-braces indicating its position within this list.

Humanoid robots and Orthotic and Prosthetic (O&P) robotic appendages that can truly mimic human movement patterns have not yet been developed and necessitate fundamental improvements in hardware and control design {1,2}. For this class of robotic devices it is not meaningful to track a small set of predetermined joint trajectories {3}. Moreover, without an attachment base securely bolted to the ground, postural balance is considered a primary control task {4}.

General, precise and practical formulation of postural stability as a control problem remains elusive {5,6}. Many studies of repetitive motions utilize return map analyses a posteriori to tackle stability in a plant/task/condition (and particular target trajectories) specific manner. However, there are many potential plants, tasks and transitions as well as external world conditions. Hence, it seems beneficial, if not necessary, for an online controller to exploit an on-line biomechanically inspired optimization strategy where joint angle trajectories are varied to achieve whole-body postural balance. In this provisional patent we present several embodiments of biomimetic motion and balance controllers.

SUMMARY OF THE INVENTION

The following summary provides a simplified introduction to some aspects of the invention as a prelude to the more detailed description that is presented later, but is not intended to define or delineate the scope of the invention.

Due to the high dimensionality of the plant being controlled, the general, non-linear and non-convex optimization problem has to be simplified so that the motion controller may operate in real-time. In the detailed description that follows, four different embodiments of motion controllers are disclosed that achieve the needed simplification.

The first of these, called Motion Control Embodiment 1, reduces the dimension of joint state space by utilizing biomechanically inspired motion primitives.

The second of these, Motion Control Embodiment 2, utilizes a quadratic proportional-derivative (PD) controller which employs a two-stage linearization method, applies constraints to variables for dynamic stability, and employs a corrective "sliding control" mechanism to account for errors in the linear model used.

Motion Control Embodiment 3 employs a non-prioritized balance control approach, with enforced linear dynamics, with all control variables truncated to linear terms in joint jerks, and with support for base planning during ground and flight locomotory phases.

Finally, we describe Motion Control Embodiment 4, a biomimetic motion and balance controller) based on center of mass (CM) energetic and biomimetic zero moment conditions.

Motion Control Embodiment 2 is the preferred embodiment. This embodiment controls the motion of an artificial appendage mechanism in either an artificial appendage or a humanoid robot. The controlled mechanism comprises multiple articulated elements that are connected at one or more joints. A controller processes current state input data indicating the current dynamic state of the mechanism and as well as desired state input data indicating the desired dynamic state of the mechanism, and produces output element acceleration data that indicates the amount by which the movements of at least some of the elements about the joints should be accelerated so that the current dynamic state is altered to more nearly conform to the desired dynamic state.

The preferred embodiment employs a stored linear model of the inverse dynamics of the controlled mechanism which defines a relationship between the element and joint accelerations that is employed to convert the output element acceleration data from the controller into computed joint acceleration data that is used to control the operation of the joints in the mechanism. The preferred embodiment may also use a stored model of the inverse kinematics of the mechanism.

In the preferred embodiment, the controller may take the form of a linear quadratic controller that further processes constraint data specifying permitted ranges of values for one or more parameters in a group of parameters consisting of output element accelerations, velocities, and positions; joint element accelerations, velocities, and positions; and joint torques. The constraint data may specify limits for the angular position for one or more of the joints and.or limits for the torque applied to one or more of the joints. The constraint data may include the restriction that specified elements be positioned within predetermined regions relative to other elements, such as the restriction that the system's Zero Moment Point be within a restricted region.

In the preferred embodiment, the output element acceleration data produced by the controller indicates the amount by which the center of mass of at least selected elements should be accelerated, and/or the amount by which the combined center of mass of one of, some of, or all of said elements should be accelerated. The controller may process the supplied input data to control one or more of the following:

(a) the center of mass position for the overall controlled mechanism, (b) the roll, pitch and yaw angle for the body supported by mechanism, (c) the roll, pitch and yaw angle of a foot element as it swings between contact positions on a support surface, (d) the angular momentum about the center of mass, and/or (e) quantities representing control goals, including sacrificing lower priority goals in favor of higher priority goals, such as temporarily sacrificing the goal of controlling angular momentum about the center of mass in favor of controlling center of mass position.

In order to compensate for errors in the stored linear model of the appendage, the controller employed in the preferred embodiment processes in input data in substeps: First, the controller issues control commands based on the computed joint torque data to control the operation of the joints. Tracking data is then acquired which indicates of the difference between the current dynamic state of the mechanism controlled by the control commands and the desired dynamic state, and the controller employs a sliding control technique to issue corrective commands based on the tracking error data directly to the joints to further modify the current dynamic state of the appendage.

The present invention provides significant advantages and improvements over existing methods, including the following:

A. The systems do not specify detailed reference trajectories;

B. Control set points are expressed in terms of a few, key high-level quantities, like center-of-mass positions and velocities, rather than in specifying joint space quantities. Complex joint trajectories emerge automatically from these high-level specifications.

C. The controllers are based on biomechanical principles and produce biomimetic motions.

BRIEF DESCRIPTION OF THE DRAWINGS

In the detailed description which follows, frequent reference will be made to the attached drawings, in which.

DETAILED DESCRIPTION

Technical Description

Figure 1:
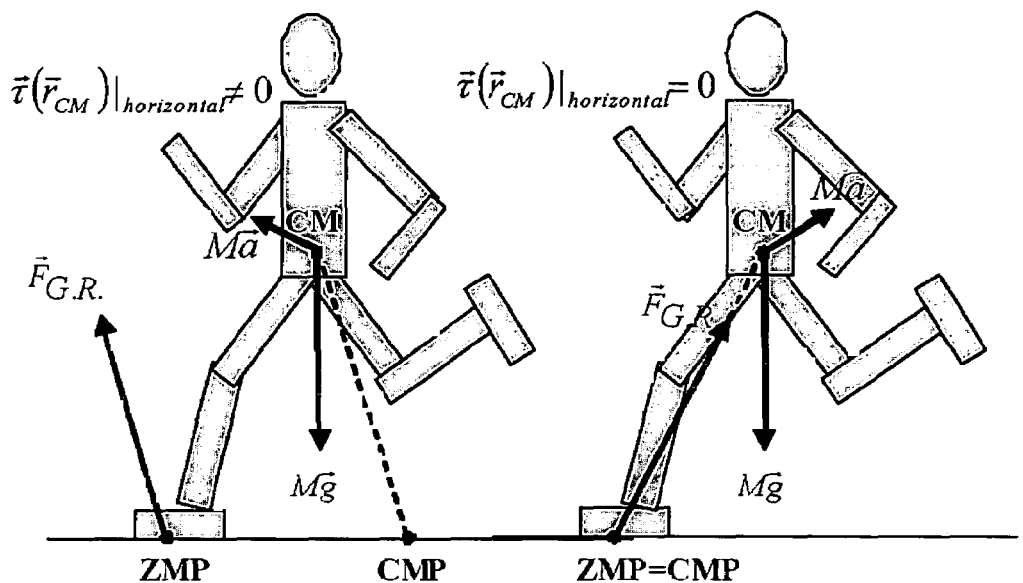
FIG. 1 illustrates the location of the Centroidal Motion Point.

Often, due to the high dimensionality of the plant being controlled, the general, non-linear and non-convex optimization problem has to be simplified so that the controller may operate in real-time. One approach is to reduce the dimension of joint state space by utilizing biomechanically inspired motion primitives {7} as described in below for the Motion Control Embodiment 1. Another approach is a hard-coded hierarchical or prioritized control {8-10}. Here the controller, local in time, first satisfies the most important task and then continues down a predetermined priority list. The quadratic-programming based version of this method was recently utilized for non-contact limb balancing {11} in combination with two-stage feedback linearization, constraints used for dynamic stability, and a sliding control framework to account for model error (see the description of Motion Control Embodiment 2). We next describe a non-prioritized balance control approach {12}, with enforced linear dynamics and all control variables truncated to linear terms in joint jerks, also utilized for support base planning during ground and flight locomotory phases (Motion Control Embodiment 3). Finally, we outline a biomimetic motion and balance controller (Motion Control Embodiment 4) based on CM energetic and biomimetic zero moment conditions.

Background: Angular Momentum in Human Walking

Biomechanical investigations have determined that for normal, level-ground human walking, spin angular momentum, or the body's angular momentum about the center of mass (CM), remains small through the gait cycle. Researchers discovered that spin angular momentum about all three spatial axes was highly regulated throughout the entire walking cycle, including both single and double support phases, by observing small moments about the body's CM {13} and small spin angular momenta {14, 15}. In the latter investigations on spin angular momentum, a morphologically realistic human model and kinematic gait data were used to estimate spin angular momentum at self-selected walking speeds. Walking spin values were then normalized by dividing by body mass, total body height, and walking speed. The resulting dimensionless spin was surprisingly small. Throughout the gait cycle, none of the three spatial components ever exceeded 0.02 dimensionless units.

To determine the effect of the small, but non-zero angular momentum components on whole body angular excursions in human walking, the whole body angular velocity vector can be computed, or $$\vec{\omega}(t) = \overleftrightarrow{I}^{-1}(\vec{r}_{CM}, t).$$

Here the time dependent quantity, $$\overleftrightarrow{I}(\vec{r}_{CM}, t) = \sum_{i=1}^{N} \overleftrightarrow{I}_i(\vec{r}_{CM}, t), \quad \text{Equation (1a)}$$

is the whole body inertia tensor about the CM. Subsequently, the whole body angular velocity vector may be integrated to give the whole body angular excursion vector, or $$\vec{\theta}(t) = \int_{-\infty}^{t} \vec{\omega}(t^*) dt^* + C \quad \text{Equation (1b)}$$

where C is an integration constant determined through an analysis of boundary conditions {14}.

The whole body angular excursion vector can be accurately viewed as the rotational analog of the CM position vector (i.e. note that analogously $$\vec{v} = \dot{\vec{r}}_{CM} = M^{-1}\vec{p}$$

and $$\vec{r}_{CM}(t) = \int_{-\infty}^{t} \vec{v}_{CM}(t^*) dt^* + D \bigg).$$

In recent biomechanical investigations, angular excursion analyses for level ground human walking showed that the maximum whole body angular deviations within sagittal (<1o), coronal (<0.2o), and transverse (<2o) planes were negligibly small throughout the walking gait cycle {14, 15}. These results support the hypothesis that spin angular momentum in human walking is highly regulated by the central nervous system (CNS) so as to keep whole body angular excursions at a minimum.

According to Newton's laws of motion, a constant spin angular momentum requires that the moments about the CM sum to zero. During the flight phase of running or jumping, angular momentum is perfectly conserved since the dominant external force is gravity acting at the body's CM. However, during the stance period, angular momentum is not necessarily constant because the legs can exert forces on the ground tending to accelerate the system {16-20}. Hence, a legged control system must continually modulate moments about the CM to control spin angular momentum and whole body angular excursions. For example, the moment about the CM has to be continually adjusted throughout a walking gait cycle to keep spin angular momentum and whole body angular excursions from becoming appreciably large. To address spin angular momentum and the moment about the CM in connection with various postural balance strategies, the CMP ground reference point was recently introduced {21-22, 14}. Goswami and Kallem (2004), {6}, proposed the same point in an independent investigation.

Background: Centroidal Moment Point

The Centroidal Moment Pivot (CMP) {23} is defined as the point where a line parallel to the ground reaction force, passing through the CM, intersects with the external contact surface (see FIG. 1). This condition can be expressed mathematically by requiring that the cross product of the CMP-CM position vector and the ground reaction force vector, $F_{G.R.}$, vanishes, or $$(\vec{r}_{CMP} - \vec{r}_{CM}) \times \vec{F}_{G.R.} = 0 \text{ and } z_{CMP} = 0. \quad \text{Equation (2)}$$

By expanding the cross product of equation (2), the CMP location can be written in terms of the CM location and the ground reaction force, or $$x_{CMP} = x_{CM} - \frac{F_{G.R.X}}{F_{G.R.Z}} z_{CM} \quad \text{Equation (3)}$$

and $$y_{CMP} = y_{CM} - \frac{F_{G.R.Y}}{F_{G.R.Z}} z_{CM}.$$

As noted by {23}, the Zero Moment Point (ZMP) {24-25}, can be expressed as a function of the CM position, net CM force ($\vec{F} = M\vec{a}_{CM}$), and net moment about the CM, $\vec{\tau}(\vec{r}_{CM})$, $$x_{ZMP} = x_{CM} - \frac{F_x}{F_z + Mg} z_{CM} - \frac{\tau_y(\vec{r}_{CM})}{F_z + Mg} \quad \text{Equation (4)}$$

and $$y_{ZMP} = y_{CM} - \frac{F_y}{F_z + Mg} z_{CM} + \frac{\tau_x(\vec{r}_{CM})}{F_z + Mg}.$$

Therefore, the CMP location may also be expressed in terms of the ZMP location, the vertical ground reaction force, and the moment about the CM, or $$x_{CMP} = x_{ZMP} + \frac{\tau_y(\vec{r}_{CM})}{F_{G.R.Z}} a \quad \text{Equation (5)}$$

and $$y_{CMP} = y_{ZMP} - \frac{\tau_x(\vec{r}_{CM})}{F_{G.R.Z}}.$$

FIG. 1 illustrates the Centroidal Moment Pivot (CMP). The CMP is the point on the support surface where the ground reaction force would have to act to keep the horizontal component of the whole body angular momentum constant. When the moment about the CM is zero (shown to the right in FIG. 1), the CMP coincides with the ZMP. However, when the CM moment is non-zero (shown on the left in FIG. 1), the extent of separation between the CMP and ZMP is equal to the magnitude of the horizontal component of moment about the CM, divided by the normal component of the ground reaction force.

As is shown by equation (5), when the CMP is equal to the ZMP, the ground reaction force passes directly through the CM of the body, satisfying a zero moment or rotational equilibrium condition. In distinction, when the CMP departs from the ZMP, there exists a non-zero body moment about the CM, causing variations in whole-body, spin angular momentum. While by definition the ZMP cannot leave the ground support base, the CMP can—but only in the presence of a significant moment about the CM. Hence, the notion of the CMP, applicable for both single and multi-leg ground support phases, is that it communicates information about whole body rotational dynamics when supplemented with the ZMP location (excluding body rotations about the vertical axis).

Background: Zero-Moment Balance Strategy

It has been suggested in the literature that postural stability during single support will be ensured if the ZMP remains at the center of the ground support envelope {24-28}. However, it is noted here that accurately controlling the ZMP location to coincide with the center of the ground support envelope will not in itself guarantee postural stability for all legged control problems. To clarify this point, consider the simple model of single support standing shown in FIG. 2A. The mass of the body is represented as a point mass attached to a massless foot and leg linkage, and the ankle is the only actuated degree of freedom.

Figure 2:
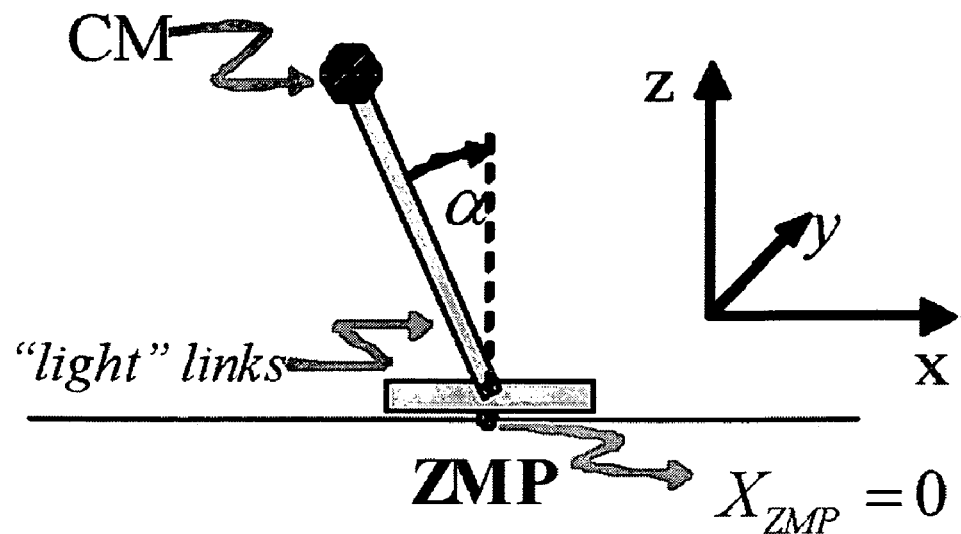
FIG. 2 illustrates the forces on a single leg model acting through a Zero Moment Point (ZMP)
Figure 2:
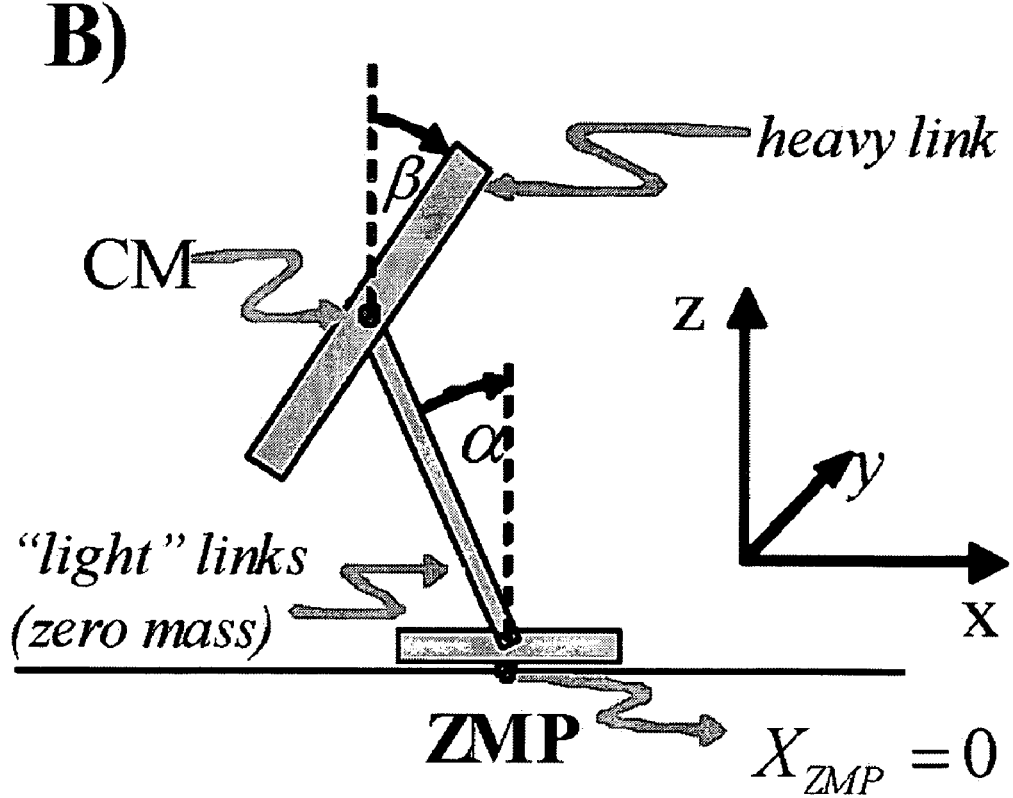

At the top of FIG. 2, at (A), a simple model of single-leg standing is shown consisting of three links: 1) a body link represented by a point mass equal to total body mass; 2) a massless leg link representing the stance leg; and 3) a massless foot link (base of support), which is aligned with the ground and which has limited extent. The ankle joint between the foot link and the leg link is the only actuated degree of freedom in the model. In (B), the same model as in (A) is shown except the body link is modeled as a solid uniform rod. In contrast to the model of (A), the model of (B) has an actuated ankle and hip joint. Thus, this model may have a non-zero moment about its CM.

If the ZMP is tightly controlled to operate at the center of the ground support envelope, such that $x_{ZMP}=0$, then according to equation (4)

$$F_x = M\ddot{x}_{CM} = M(\ddot{z}_{CM} + g)\frac{x_{CM}}{z_{CM}} - \frac{\tau_y}{z_{CM}}. \quad \text{Equation (6)}$$

For this simplified model, the moment about the CM is always equal to zero, $\tau_y = 0$, since the mass of the body is represented as a single point mass. Thus, from equation (6) we have $$\ddot{x}_{CM} = (\ddot{z}_{CM} + g)\frac{x_{CM}}{z_{CM}}. \quad \text{Equation (7)}$$

We see from equation (7) that for this simplified model, a control system that maintains the ZMP position at the center of the ground support envelope, or $x_{ZMP}=0$, causes the system to be equivalent to a statically unstable, non-actuated inverted pendulum. Thus, we may conclude that controlling the ZMP to operate at the center of the ground support envelope during single support cannot, by itself, ensure postural stability.

If we now allow for non-zero ZMP positions, we obtain $$\ddot{x}_{CM} = (\ddot{z}_{CM} + g)\frac{x_{CM} - x_{ZMP}}{z_{CM}} \quad \text{Equation (8)}$$

Thus, we see from equation (8) that by selecting an appropriate non-zero ZMP trajectory, the model of FIG. 2A can be stabilized albeit for relatively modest CM disturbances. Here stability refers to the capacity of the system to restore the CM to a location vertically above the center of the ground support envelope ($x_{ZMP}=0$) after a perturbation. For example, if the CM projection onto the ground extends beyond the boundaries of the foot as a result of a disturbance to the system, the system cannot be stabilized simply by controlling ZMP position because the foot is not physically attached to the ground surface (see equation (8)) {29, 11, 30}.

Although controlling ZMP position is one strategy for stabilizing legged posture, it is not the only tool for addressing stability. For example, during single-leg standing, consider shrinking the stance foot to a single point. The ZMP is then constrained at that contact point and cannot be repositioned using a ZMP control strategy. As is apparent from equation (6), the only way to stabilize such a system is to produce a non-zero moment about the CM. As argued in {23} by controlling both the ZMP and CMP ground reference positions, overall postural stability during single support standing can be maintained even in the presence of large disturbances where the CM projection on the ground surface extends beyond the ground support envelope.

Background: Moment Balance Strategy

As noted in {23}, the CMP trajectory was confined to the ground support base for each subject and for each walking trial. Thus, one metric of human-like walking that may be useful in the evaluation of biomimetic humanoid robots is that the CMP must remain within the ground support base, near the ZMP, throughout the entire gait cycle. However, a zero moment about the CM, or a zero CMP-ZMP separation, should only be viewed as a condition of body rotational equilibrium and not a condition of postural stability. A loss of rotational equilibrium does not necessarily mean that the person or robot is destined to fall. In fact, the moment about the CM is prominently non-zero for many stable legged movement patterns {16-20}. Non-zero CM moments are expected since the application of CM moment by a legged control system can increase the restoring force applied to the CM, as shown by equation (6), restoring CM position to a desired location {14,30,11}.

Since the application of moments about the CM is one critical control strategy to achieve postural stability in the presence of disturbances, the objective for the controller of whole-body angular behavior should not be to achieve a zero CM moment, or equivalently, a zero CMP-ZMP separation. Rather, a CM moment should be applied by the system controller to achieve a desired spin angular momentum and a particular whole-body angular excursion (see equation (1)). For example, focusing solely on rotational degrees of freedom, one could write a simple $2^{nd}$ order differential control equation for a desired target moment, or $$\vec{\tau}_{des.}(\vec{r}_{CM}) = \dot{\vec{L}}_{des.} + \vec{a}\Delta\vec{\theta} + \vec{b}\Delta\vec{\dot{\theta}} = \dot{\vec{L}}_{des.} + \vec{a}\Delta\vec{\theta} + \vec{b}'\Delta\vec{L}(\vec{r}_{CM}) \quad \text{Equation (9)}$$

where $\Delta\vec{L}(\vec{r}_{CM}) = \vec{L}(\vec{r}_{CM}) - \vec{L}_{des.}(\vec{r}_{CM})$ and $\Delta\vec{\theta} = \vec{\theta} - \vec{\theta}_{des.}$, $\vec{a}$ and $\vec{b}$ (with $\vec{b}' = \vec{b}\,\vec{I}^{-1}(\vec{r}_{CM})$) are second order tensors, i.e. 3×3 matrices representing rotational "stiffness" and "damping" coefficients respectively, $$\vec{I}(\vec{r}_{CM}) = \sum_{i=1}^{N} \vec{I}_i(\vec{r}_{CM})$$

is the whole body moment of inertia tensor about the CM (also a function of time) and $\vec{\omega} = \vec{I}^{-1}(\vec{r}_{CM})\vec{L}(\vec{r}_{CM})$ is the whole body be integrated to give θ), see equation (1).

Alternatively, instead of whole body angular excursions, which are not directly measurable quantities, one may consider using whole body principal angles defined by the relative orientations of the principal axes of the whole body moment of inertia tensor with respect to the non-rotating lab frame axes {12}. For a humanoid walking robot, the desired whole body angular excursion and the spin angular momentum would both be set to zero and the rotational stiffness and damping coefficients would then be adjusted to achieve a desired system response.

In his book, *Legged Robots that Balance*, Raibert (1986), {17}, speculated that a control system that keeps angular momentum constant during stance could achieve higher efficiency and better performance. Motivated by biomechanical measurements showing the relatively small size of CM moments during human walking, Popovic, Gu and Herr (2002), {13}, suggested that humanoid control systems should explicitly minimize global spin angular momentum during steady state forward walking ($\vec{L}_{des}(\vec{r}_{CM})=0$). Using this approach, the zero-spin controller would apply corrective moments to minimize body spin when the whole body state is such that spin is non-zero. It is noted here that a consequence of this control objective is that the CMP-ZMP separation distance is minimized. However, a control system that only minimizes the CMP-ZMP separation distance will only ensure a constant spin angular momentum and not specifically a zero spin value.

Kajita et al. (2003; 2004), {31-32}, implemented a zero-spin control on the humanoid robot HRP-2 and showed its usefulness in kicking, hopping and running. Still further, Popovic, Hofmann and Herr (2004a), {14}, showed in a 2-D numerical simulation of walking that biologically realistic leg joint kinematics emerge through the minimization of spin angular momentum and the total sum of joint torque squared (minimal effort criteria), suggesting that both angular momentum and energetic factors may be important considerations for biomimetic controllers.

As noted in {23} controlling both ZMP and CMP enhance postural stability. For the simplified model of single-leg standing shown in FIG. 2A, ankle torques have to be applied to move the ZMP such that appropriately needed horizontal forces are generated, as dictated by equation (8), to move the model's CM back over the foot support envelope. However, as required by physics and noted in {23}, the ZMP cannot leave the ground support base. This physical constraint poses a restriction on the magnitude of the restoring CM forces that can be applied by the system controller to restore CM position, and therefore, directly limits the range of perturbation that can be rejected by the system.

Let us now relax the zero moment condition (CMP=ZMP) and consider the model shown in FIG. 2B. In that model, the point mass of model 2A is replaced with a uniform rod that rotates about a hip joint at the top of a massless leg and foot linkage. By controlling both the ZMP and CMP trajectories, a larger set of perturbations can be rejected than when controlling only the ZMP trajectory {14, 30, 11}. Even when the ZMP is at the very edge of the ground support envelope in the model of FIG. 2B, a horizontal restoring force can still be produced through the application of a moment about the CM, or equivalently by controlling the CMP relative to the ZMP. According to equation (4), the horizontal restoring force output of the model shown in FIG. 2B can now be written as $$F_x = M\ddot{x}_{CM} \qquad \text{Equation (10)}$$
$$= M(\ddot{z}_{CM} + g)\frac{x_{CM} - x_{ZMP}}{z_{CM}} - \frac{\tau_y}{z_{CM}}$$
$$= F_x^{zero\text{-}moment} + F_x^{moment}$$

where $$F_x^{zero\text{-}moment} = M(\ddot{z}_{CM} + g)\frac{x_{CM} - x_{ZMP}}{z_{CM}}$$

corresponds to a Zero-Moment Balance Strategy and $$F_x^{moment} = -\frac{\tau_y}{z_{CM}}$$

corresponds to a Moment Balance Strategy. Because the CMP represents a unique pivot point, equation (10) may be written more compactly as $$F_x = M(\ddot{z}_{CM} + g)\frac{x_{CM} - x_{ZMP}}{z_{CM}} \qquad \text{Equation (11)}$$

As highlighted by equation (11), the CM restoring force can be controlled by modulating the separation distance between the CM projection on the ground surface and the CMP location.

Depending on the character of a particular movement task and robotic structure, the two balance control strategies may have different levels of influence on postural stability. For example, in FIG. 2B, if the model's foot link were made infinitely small, with $x_{ZMP}=0$ as a physical constraint, the Moment Balance Strategy (CMP≠ZMP) would necessarily dominate. However, when the CMP is in the vicinity of the ground support envelope boundary during single-leg balancing, or outside that boundary, the Moment Balance Strategy (CMP≠ZMP) must dominate since ZMP trajectory control alone cannot restore postural balance {14, 30, 11}. Therefore, the CMP location relative to the ground support envelope is an important indicator for a control system to determine which balance strategy should necessarily dominate {14, 30, 11}.

EMBODIMENTS OF THE INVENTION

Due to the high dimensionality of the plant being controlled, the general, non-linear and non-convex optimization problem has to be simplified so that the motion controller may operate in real-time.

One approach is to reduce the dimension of joint state space by utilizing biomechanically inspired motion primitives {7} as described below for Motion Control Embodiment I.

Another approach is a hard-coded hierarchical or prioritized control {8-10}. Here the controller, local in time, first satisfies the most important task and then continues down a predetermined priority list. The quadratic-programming based version of this method was recently utilized for non-contact limb balancing {11} in combination with two-stage feedback linearization, constraints used for dynamic stability, and sliding control framework to account for model error and is presented below as Motion Control Embodiment II.

We further describe Motion Control Embodiment III. a non-prioritized balance control approach {12}, with enforced linear dynamics and all control variables truncated to linear terms in joint jerks, also utilized for support base planning during ground and flight locomotory phases.

Thereafter, we outline a biomimetic motion and balance controller (Motion Control Embodiment IV) based on CM energetic and biomimetic zero moment conditions.

Embodiment 1

Motion Control Based on Angular Momentum Primitives

To deal with the complexity of humanoid movements, a reduced order control architecture is needed. Recently, the concept of motor primitives has been discussed in the literature in the context of dimensional reduction. Experiments involving multiple point stimulation of a frog's spinal cord {33} demonstrated that a limb's endpoint generated force field obeys the principle of superposition. Moreover, only a small set of primitive force fields was sufficient to explain a large data sample {33}. These findings support the hypothesis that the central nervous system may generate a wide repertoire of motor behaviors through the vectorial superposition of a few motor primitives stored within the neural circuits in the spinal cord. Experiments on human reaching movements {34} gave further support for this concept. Theoretical studies {35} correlated the system's ability to learn with the actual functional form of its dynamic primitives. The kinematics trajectories of a planar human arm have been studied {36} and motor movement primitives have been obtained based on the principal component decomposition of these trajectories. A similar method has been used for humanoid 3D upper body controllers {37}. The motion primitives were first extracted and then used for control with a small set of basic controllers {37}.

In this motion control embodiment, the motor primitives approach is used for the first time to analyze whole body movements and subsequently generate novel motions. Moreover, this is the first study where a body segments' spin angular momentum distribution is used to generate motor primitives. Motivation for this approach came from the evidence that for a large class of activities, such as balancing while standing, walking and running, the human body closely regulates total spin angular momentum {13-14, 29}.

Biomechanics—Methods: Kinematic Gait Analysis

Ground reaction forces, center of pressure (CP) trajectory and kinematic data describing human limbs during walking were obtained in the Gait Laboratory of Spaulding Rehabilitation Hospital, Harvard Medical School. The healthy normal subject walked at slow and self-selected moderate speeds for seven trials each. The ground reaction forces were measured using 2 AMTI forceplates (model OR6-5-1, AMTI, Newton, Mass.) at the frequency of 1080 Hz. The forceplates had a precision of approximately 0.1 Newton. The limb trajectories were acquired using an infrared VICON Motion Capture system (VICON 512, Oxford Metrics, Oxford, England). Thirty-three markers were placed on the subject's body: sixteen lower body markers, five trunk markers, eight upper limb markers and four head markers. Motion data were gathered at a frequency of 120 Hz. Depending on the position and movements of the subject, the VMC could detect the marker positions with a precision of a few millimeters.

Figure 3:
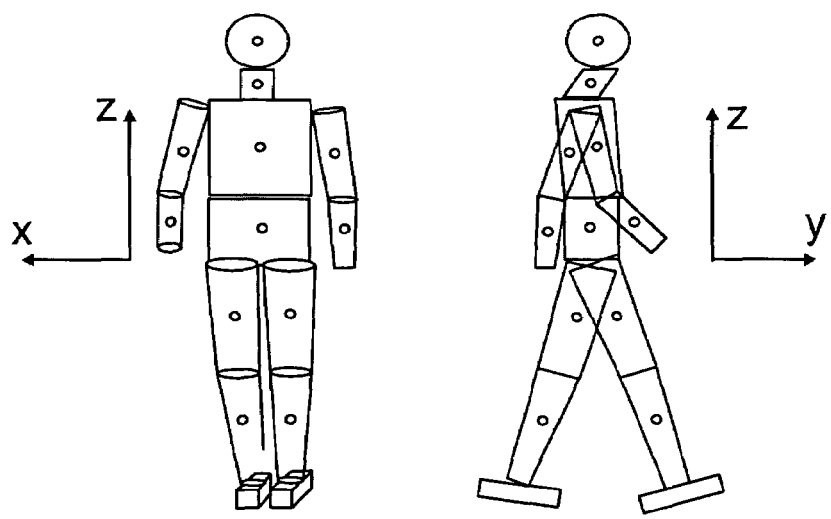
FIG. 3 shows a human model consisting of 16 links used for gait analysis.

The human model used for gait analysis consisted of 16 links: right and left feet, shanks, thighs, hands, forearms, upper arms, the pelvis-abdomen region, the thorax, the neck and the head. The feet and hands were modeled as rectangular boxes. The shanks, thighs, forearms and upper arms were modeled as truncated cones. The pelvis-abdomen link and the thoracic link were modeled as elliptical slabs. The neck was modeled as a cylinder and the head was modeled as a sphere. This model is shown in FIG. 3. About twenty physical measurements of the subject's links dimensions were taken to accurately model the subject. Based on the links' dimensions the link's masses and densities were modeled to closely match the experimental values {38-39}. The human model had a total of 38 degrees of freedom; 32 internal degrees of freedom (12 for the legs, 14 for the arms and 6 for the rest) and 6 external degrees of freedom.

As illustrated in FIG. 3, a human model consisting of 16 rigid links was used to calculate the distribution of the angular momentum throughout the human body from the gait data. The angular momentum about the body's CM of each link was calculated as a sum of the orbital and spin components. The orbital component was given as the angular momentum in the body's CM frame of the point mass located at the link's CM with the mass equal to that of the link. The spin component was the angular momentum of the link in the link's CM frame.

Principal component analysis (PCA) was performed on each links' angular momentum, for each of the three spatial components, to give the angular momentum primitives. The eigenvalue problem of the 16 by 16 (16 was the number of links of our human model) data covariance matrix was solved. The eigenvectors were then ordered by the respective size of their eigenvalues. In this way a new 16-dimensional basis was obtained where basis vectors, $\vec{P}_i$, were linearly independent and ordered by their statistical, i.e. data dependent, significance. In principle, only some basis vectors were utilized to reproduce the initial data set at chosen level of precision.

The actual time dependent normalized distribution, $c_i(t)$, of each PC vector $\vec{P}_i$ as a function of the gait cycle was then obtained by the projection method. The projection method finds the scalar product of the ith PC, $\vec{P}_i$, and the normalized gait spin distribution $\vec{L}(t)/|\vec{L}(t)|$ both represented in the original links' angular momentum basis. The time dependent normalized distribution coefficients satisfy $$\sum_{i=1}^{16} c_i^2(t) = 1 \qquad \text{Equation (12)}$$

Biomechanics—Results: Angular Momentum Primitives

The first principal components, i.e. angular momentum primitives, in the sagittal, coronal and transverse planes explained approximately 90%, 75% and 85% of the data, respectively. The first three primitives in each plane combined explained 99%, 95%, and 95% of the data, respectively. To compare the PCs of two different speeds their scalar product was found. The scalar product of the first primitives, of the same subject, at slow and moderate walking speeds was larger than 0.99 for all three spatial directions. The scalar product of the second primitives at these same walking speeds was only slightly smaller, or 0.99, 0.98, and 0.97 for sagittal, coronal and transverse plane rotations, respectively. These observations suggest that the angular momentum primitives are largely invariant to walking speed.

Figure 4:
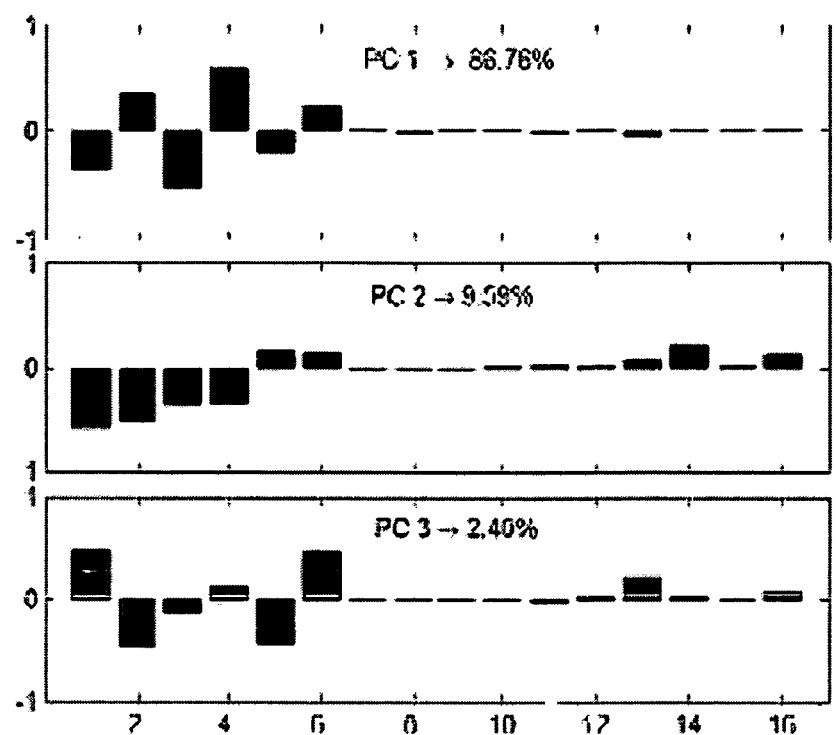
FIG. 4 depicts the first three angular momentum primitives in the sagittal plane and their respective data.
Figure 5:
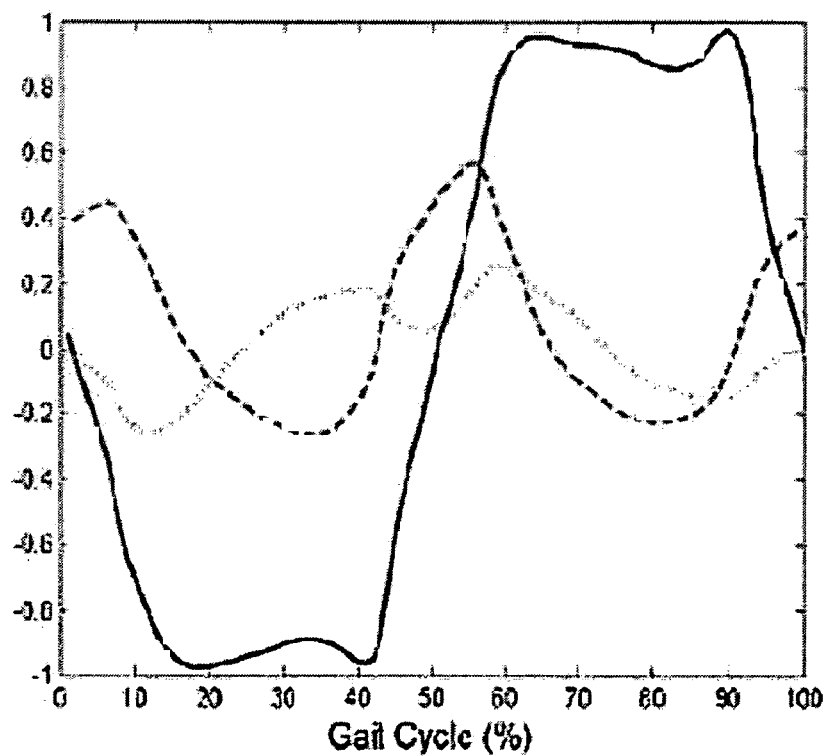
FIG. 5 shows the average distribution of the first three angular momentum primitives as a function of the percentage of the gait cycle.

FIG. 4 shows the first three angular momentum primitives, with largest data explained. FIG. 5 shows their average normalized distributions, $c_1(t)$, $c_2(t)$ and $c_3(t)$, and as a function of the percentage of the gait cycle. In addition to these findings we have also observed that the first three primitives' distributions for slow speed, $c_i^{sl}(t)$, and moderate speed, $c_i^{mo}(t)$, of the same subject overlap at one standard deviation throughout the whole gait cycle with standard deviations on the order of several percent from the mean value. The speed invariance of the PC and their gait cycle dependent normalized distributions makes angular momentum primitives a useful tool for gait synthesis.

FIG. 4 illustrates the first three angular momentum primitives in the sagittal plane and their respective data. The abscissa numbers and human model links are paired in the following order: left foot (1), right foot (2), left shin (3), right shin (4), left thigh (5), right thigh (6), left hand (7), right hand (8), left forearm (9), right forearm (10), left upper arm (11), right upper arm (12), abdomen and pelvis (13), thorax (14), neck (15) and head (16).

FIG. 5 shows the average distribution of the first three angular momentum primitives as a function of the percentage of the gait cycle. By convention, 0% and 100% represent consecutive heel strikes of the same foot. The first primitive with largest data explained is represented with solid line, the second primitive with a dashed line and the third primitive with a dotted line.

Control Algorithm

Towards the final goal of developing a biomimetic walking robot, the angular momentum primitives were used to define the motion of a humanoid model following a simple predefined CM trajectory of constant height and speed. Our control system searches for joint reference trajectories that minimize the error between the model's angular momentum distribution and the biologically determined distribution.

As utilized for this controller, given the stride length and walking speed the position in the human gait cycle can be very precisely determined based only on the CM position in respect to the stance foot. This is because the CM deviates only slightly around the point that is moving with constant forward speed. After the estimate on position in the gait cycle was made, the results presented in FIGS. 4-5 were used to determine desired biomimetic spin distribution.

The eight degree of freedom (DOF) humanoid model utilized to test this control architecture consisted of eight rigid links or appendages: a pair of feet, a pair of shanks, a pair of thighs, a pelvis and abdomen as one link and a thorax. The model moved in the sagittal plane only and had one non-rotating stance foot at all time. This gave the model effectively seven DOF.

Figure 6:
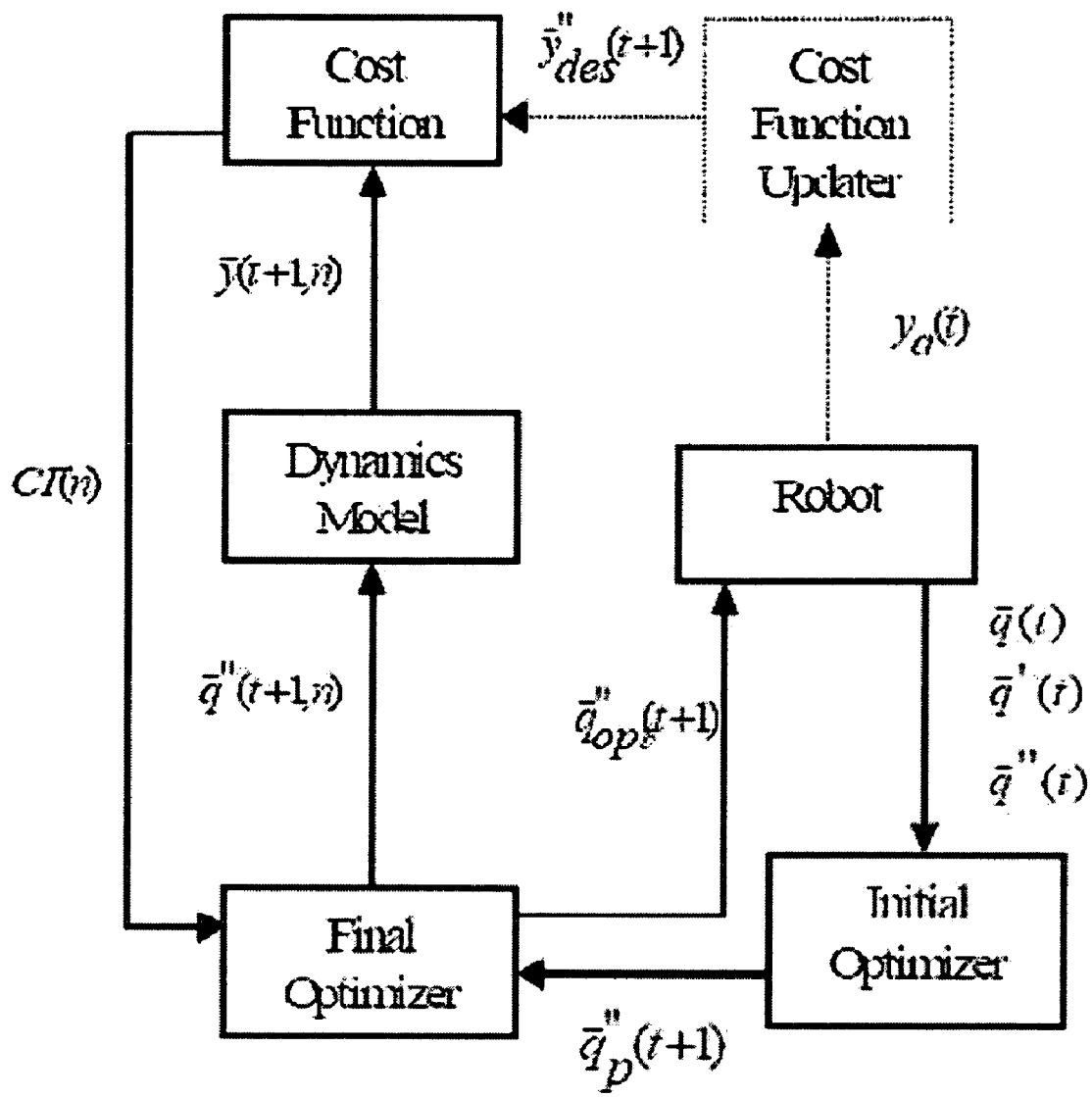
FIG. 6 illustrates the control method employed for Embodiment 1 of the invention.

FIG. 6 illustrates the control method employed for our current simulation and results. For this implementation, the Robot block and the Dynamics Model block were equivalent. The general flow of the controller is described below. Based on the robot's actual joint angles, $\vec{q}(t)$, joint angular velocities, $\vec{q}'(t)$ and joint angular accelerations, $\vec{q}''(t)$, an initial optimizer quickly determined a suggestion for the next time step's joint accelerations based on the spin distribution data. The final optimizer then finely tuned the offered solution by performing a more sophisticated search in the close vicinity of the initial optimizer's suggested joint acceleration vector for the next time step's joint accelerations. The optimization was based on minimizing the cost function from the vector of terms, $\vec{y}(t)$. These fully-optimized joint accelerations were applied to the robot. The robot's actual kinetic data then updated the cost function and simultaneously began the initial optimizer for the next time step.

The concept behind the initial optimizer is as follows. Given the estimated CM position and velocity at the next time step together with the stance foot position, the spin of the stance foot at the next time step was calculated. The controller then estimated the appropriate gait phase and used the speed invariant biological spin distribution to generate the links' desired angular momentum at the next time step. Given this desired angular momentum distribution, the joints' desired angular accelerations were determined. This solution then served as the initial guess for the final optimizer.

The procedure to generate the links' desired angular momentum consisted of optimizing the stance ankle acceleration so that the shin's angular momentum matches the desired spin. The same procedure is then applied to the knee joint, so that the stance thigh's angular momentum matched the desired one, and this was continued for all other joints. By starting with known foot dynamics the whole body spin distribution was optimized to reproduce the biological distribution. This procedure significantly simplified the process of spin distribution optimization. Instead of a complex nonlinear optimization problem defined in N-dimensional space, where N is the number of degrees of freedom, the problem is reduced to N simpler one-dimensional problems. With a 2.4 GHz PC used for our simulations, the time for obtaining the initial optimizer's solution was generally two orders of magnitude smaller than the size of the physical time step, 0.25 ms.

FIG. 6 is a block diagram of controller. The vectors $\vec{q}(t)$, $\vec{q}'(t)$ and $\vec{q}''(t)$ denote the position, velocity and acceleration of the robot's joints. The vector $\vec{y}(t)$ denotes the cost function terms to be optimized. The subscript's $\alpha$ and p denote, respectively the actual robot values and the best guess for the next joint accelerations based on the initial optimizer. The subscript n denotes the nth iteration of the optimizer. The variable CF(n) is the cost of the nth iteration of joint accelerations. The subscript des denotes the suggested change to the cost function terms based on the robot's actual response. The subscript opt denotes the lowest cost choice of new joint accelerations.

The effect of numerical errors in the estimated CM position and velocity, and errors in the appropriate gait phase estimates, was compounded for links that were further apart from the stance leg foot. In the current implementation, to increase the quality of the initial optimizer's solution, the swing leg's hip, knee and ankle joint angular accelerations were also optimized to secure foot clearance, to minimize the error between the actual and desired CM trajectory and each joint's acceleration was constrained so that the joint's angles at the next simulation step were inside the biological angle ranges. In addition, the swing leg motion was optimized to ensure that the vertical projection of the CM onto the ground was close to the center of the projected-swing-foot support polygon (PSP). The PSP was defined here as the polygon that encloses the stance foot and the vertical projection of the swing foot onto the ground. In gait studies we observed that the projected CM position always falls inside the PSP and is never too far from its center. This may represent part of the human motor control strategy for addressing small to medium size disturbances. When efforts to balance cause the swing leg to suddenly step down, it is likely to be beneficial that the CM projection is not very far from the center of the PSP so that the plant could be most efficiently stabilized.

When the starting guess was specified, the final optimizer performed a medium-local gradient based type of search in the large N dimensional space with small, limited number of search points. With a Matlab based (Mathworks, Natick, Mass.) implementation and several hundred search points this optimization took about 80 ms real processing time for the simulation's 25 ms time increment. The cost function included the sum of biologically weighted joint torques squared, where weighting factors are given by the biological peak values for the single support, the sum of joint torque derivatives squared and the desired CM position and CM velocity. The desired CM trajectory was represented as a point moving with constant speed. The cost function included very large terms to limit joint angles to biological ranges, and moderate terms to match biological spin distribution. The cost function included a term that penalized the FRI point proximity to the edge of the foot support polygon depending on the gait phase and a term that ensured the foot clearance also depending on the gait phase.

To test the appropriateness of the gradient based search performed by the final optimizer we experimented with another version of the final optimizer using the same cost function and utilizing a genetic algorithm type of search in a much larger volume of the N-dimensional space. In this case, for about $10^6$ search steps, the final optimizer's search took an order of 100 s per simulation's 25 ms time increment.

Control Results

Figure 7:
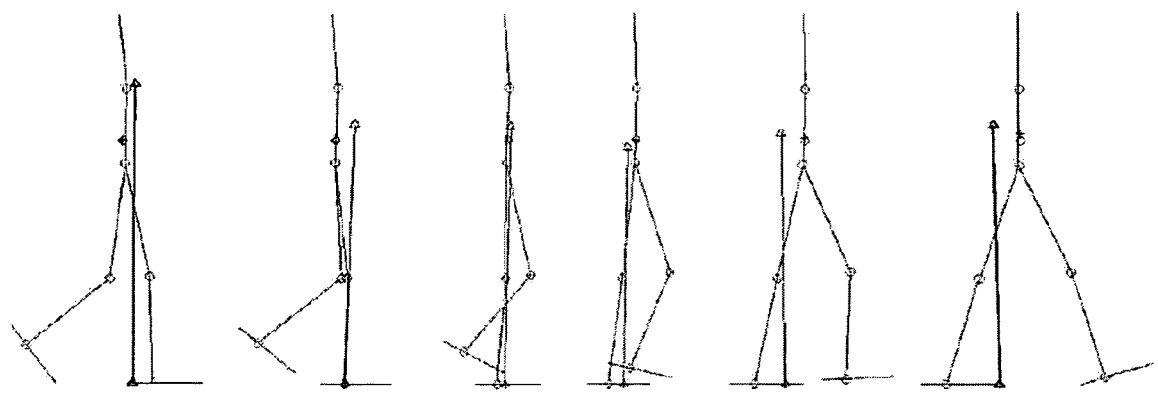
FIG. 7 shows six consecutive poses of the two-dimensional sagittal human model for the single support phase.
Figure 8:
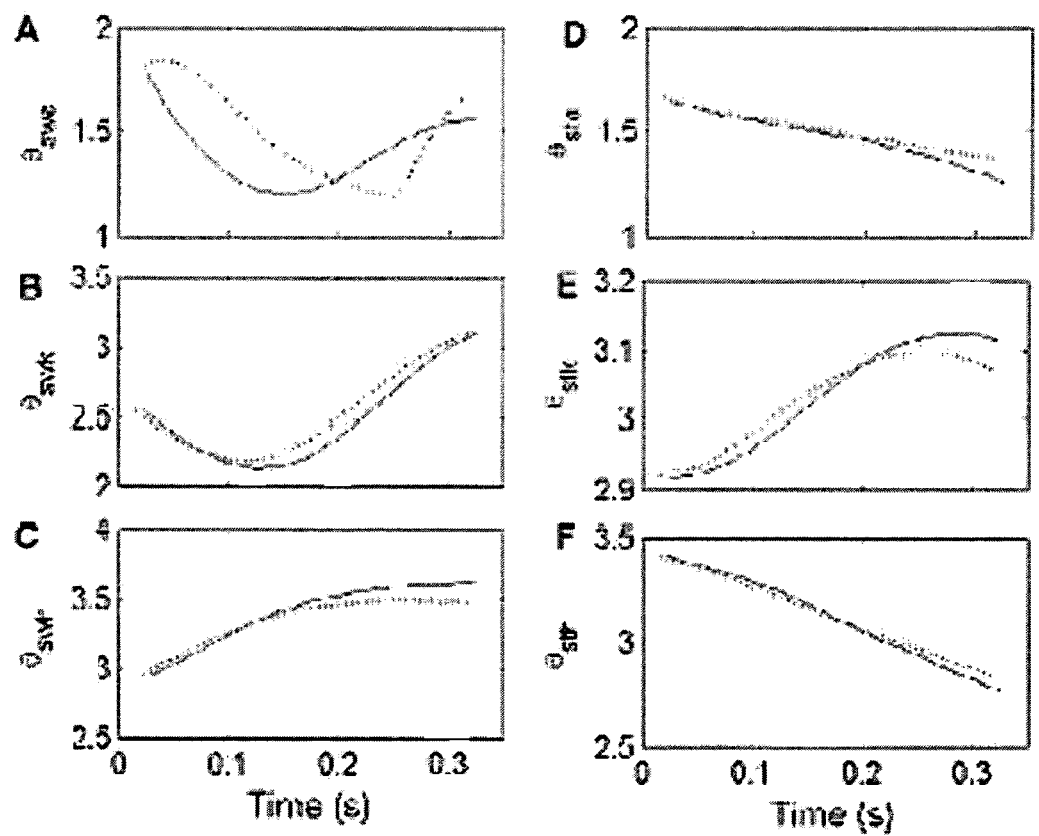
FIG. 8 shows the joint angles (hip, knee and ankle for stance and swing leg) together with the actual biological gait data for comparison.

FIG. 7 shows six consecutive poses of the two-dimensional toy sagittal human model for the single support phase using the local gradient based final optimizer. The target CM, emergent CM, emergent FRI point together with emergent ground reaction force vector are also shown. This dynamical motion was obtained using the controller with a specified initial condition obtained from the biological gait data. FIG. 8 shows the joint angles (hip, knee and ankle for stance and swing leg) together with the actual biological gait data for comparison. In FIG. 7, the target CM is represented with a cross and the actual simulation's CM is denoted with a diamond. The ground reaction force vector is represented with an arrow and it originates at the FRI point moving beneath the stance foot. The force magnitude is represented so that 1 N corresponds to 2 mm of the actual humanoid model's dimensions. Height of the CM is approximately 1 m.

FIG. 8 shows a comparison of the simulation joint angles (solid lines) with joint angles from biological gait data (dotted line). A) Swing ankle. B) Swing knee. C) Swing hip. D) Stance ankle. E) Stance knee. F) Stance hip.

When comparing the local gradient based and genetic algorithm type search used by the final optimizer for the same initial plant state and the same initial optimizer guess we observed either the results of the two methods to be almost identical with no apparent gain in using the slower genetic algorithm search or the optimization results of the two methods were very different and at successive time increments the genetic algorithm based approach began to give increasingly poor results.

Discussion

From biological gait data we observed all joints collected behavior in terms of angular momentum distribution. The collected behavior, i.e. angular momentum primitives and their respective gait dependent normalized distributions are invariant with speed. We also observed that using these angular momentum primitives reduces the dimensionality of the problem; for sagittal plane rotation we find three primitives that effectively explain all biological walking data. Based on these observations we proposed a novel control architecture.

Our current control architecture utilizes two distinct optimizers, the initial optimizer and the final optimizer. The advantage of having the initial optimizer is that it quickly generates highly biomimetic results even though no predefined joint trajectories are employed. Using the speed invariant angular momentum primitives effectively reduces the search in the large N dimensional space to N one-dimensional optimization problems. The optimization of N DOF using D search points per DOF requires $D^N$ computations. By our method, this optimization has been reduced to computations. Even with this reduction in the number of computations, an initial guess that is very close to the global minimum of the entire N-dimensional space can still be found. Having an initial guess in the vicinity of the optimal solution simplifies the final optimizer's search. The final optimizer's search can then be only medium-local and fast enough so that real time control is achievable.$^{D \cdot N}$ For the sagittal eight DOF model with known dynamics and no external disturbances, the initial optimizer gave notably biomimetic results. For this simulation the presence of the final optimizer has not offered a particular advantage to our control scheme; the visual solution of the figure walking was not different from the solution found using the final optimizer. However, for the control of a physical robot, i.e., a plant embedded in realistic conditions, we anticipate an important role for the final optimizer. The initial optimizer, using the current architecture, is most likely insufficient to reject various disturbances to the plant, so that the initial optimizer's solution will need to be improved by the final optimizer.

To further improve our control methodology we propose variations in the input spin PC distributions. One should be varying only the first three PCs about the initially estimated value, obtained by the method described earlier. For each slightly varied combination of the first three PC's one should repeat the same procedure, as with the original initial optimizer, of solving N one-dimensional problems and then obtaining the joint cost function for the whole plant. Finally, among all probed combination of the first three PC distributions one should choose the one with minimal cost. As our preliminary results suggest, this procedure eliminates errors in the initial estimation of the spin distribution and it also rejects the numerical error more robustly. With this improvement of our initial optimizer, our suggestion is to completely eliminate the final optimizer from the control loop.

For very large disturbances we anticipate a switching mechanism that will completely end the walking task and concentrate on pure balancing mechanisms. For the control of a physical robot, we anticipate having an adaptive control scheme. Also, as indicated in FIG. 6, one should consider cost function updating mechanisms that we believe should improve the quality of motion in both biomimetic and stability sense.

Embodiment 1

Advantages and Improvements

To deal with the complexity of human movements, a reduced order control architecture is needed. In this motion control embodiment, the motor primitives approach is used for the first time to analyze whole body movements and subsequently generate novel motions. Moreover, this is the first study where a body segments' spin angular momentum distribution is used to generate motor primitives. Motivation for this approach came from the evidence that for a large class of activities, such as balancing while standing, walking and running, the human body closely regulates total spin angular momentum {13-14, 29}. This optimization based control architecture easily performs in real time while yielding highly biomimetic results.

Embodiment 2

Motion Control Based on Non-Contact Limb Movements

Here, we describe the control architecture for legged systems, where the acceleration of non-contact limbs is employed as a key stabilization strategy. The controller incorporates feedback linearization, and quadratic programming-based optimal control, within a sliding control framework. The feedback linearization component decouples and linearizes the dynamics of the plant in terms of the reaction points to be controlled. The optimal controller observes constraints such as joint ranges, maximum joint torques, and the restriction that the Foot Rotation Index (FRI), {4}, is within the support polygon. The sliding control framework ensures robustness, allowing for modeling inaccuracies.

Plant Linearization

Figure 9:
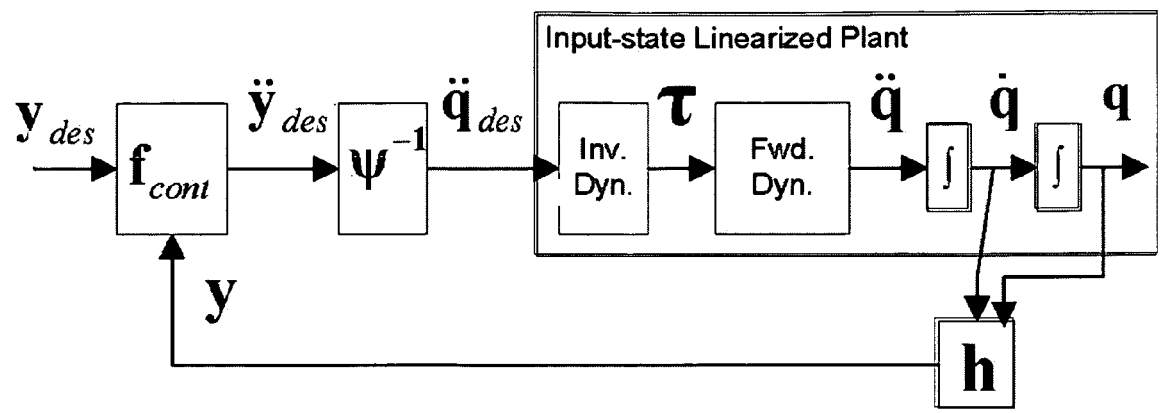
FIG. 9 depicts the feedback linearization architecture of the controller that forms Embodiment 2 of the invention.

The feedback linearization architecture of the controller is shown in FIG. 9. The purpose of the feedback linearization is to make the plant appear linear to the controller, $f_{cont}$.

The linearization is accomplished in two stages. First, the forward dynamics of the plant are linearized using an inverse dynamics model, resulting in an input-state linearized plant {40}. Thus, the plant is linear for a controller that selects desired joint accelerations. A second, geometric transform is used to convert from desired accelerations of the outputs (the reaction points) to desired joint accelerations. This transformation, indicated by $\Psi^{-1}$ in FIG. 9, is a specialized inverse kinematics transform.

Thus, using the above architecture, if we ignore joint and FRI constraints, the controller, $f_{cont}$, sees the rest of the system as being completely linearized and decoupled. Thus, simple control techniques for SISO $2^{nd}$-order linear systems (pole placement, for example) can be used within this controller.

We now discuss some details of these linearizations. The input-state linearization of the plant using inverse dynamics is straightforward. The inverse dynamics for the plant are expressed in the following standard form:

$$H(q)\ddot{q} + C(q,\dot{q})\dot{q} + g(q) = \tau \quad \text{Equation (13)}$$

where q is a vector of joint angles, $\tau$ is a vector of joint torques (the control input to the plant), H(q) is a matrix of inertial terms, $C(q,\dot{q})$ is a matrix of velocity-related terms, and g(q) is a vector of gravitational terms. Choosing equation (13), (with $\ddot{q}$ replaced by $\ddot{q}_{des}$) as the control law and substituting into the forward dynamics yields $$\ddot{q} = \ddot{q}_{des} \quad \text{Equation (14)}$$

Thus, the system is exactly linearized, and completely decoupled into a set of SISO (single input, single output) systems. This technique is sometimes called "computed torque", "inverse dynamics" or "feedforward" control in the robotics literature {41}.

This linearization is relatively straightforward due to the structure of the plant dynamics. However, the problem is not solved, because the goal is not specifically to control plant state, but rather, to control outputs derived from plant state. These outputs (CM, for example) are nonlinear functions of plant state, so a further transformation (indicated by $\Psi^{-1}$ in FIG. 9) is needed. The plant outputs (desired positions and orientations of reaction points) are given by $$y = h(q) \quad \text{Equation (15)}$$

where h is a forward kinematic transformation. Taking partial derivatives yields, for each output $y_i$ $$\dot{y}_i = \frac{\partial h_i}{\partial (q)} \dot{q} = \sum_{j=1}^{12} \frac{\partial h_i}{\partial q_j} \dot{q}_j \quad \text{Equation (16)}$$

where j indicates the joint. Differentiating this again yields $$\ddot{y}_i = \sum_{j=1}^{12} \left( \frac{\partial h_i}{\partial q_j} \ddot{q}_j + \frac{\partial^2 h_i}{\partial q_j^2} \dot{q}_j^2 + \sum_{k=j+1}^{12} 2\frac{\partial^2 h_i}{\partial q_j \partial q_k} \dot{q}_j \dot{q}_k \right) \quad \text{Equation (17)}$$

It is useful, at this point, to use spatial notation {42} to represent spatial accelerations of reaction points. With this notation, the spatial acceleration of link i of an articulated mechanism is formulated as $$\hat{a}_n = \sum_{i=1}^{n} \hat{s}_i \ddot{q}_i + \sum_{i=2}^{n} \left[ \sum_{j=1}^{i-1} \hat{s}_j \dot{q}_j \right] \hat{x} \hat{s}_i \dot{q}_i \quad \text{Equation (18)}$$

where $\hat{a}_t$ is the spatial acceleration vector, and $\hat{s}_i$ is the Jacobian column for joint i. All of these vectors are in global coordinates. The vector $\hat{s}_i$ is the local axis vector, $\hat{s}_i'$, for joint i transformed to global coordinates using the spatial transformation matrix: $_0\hat{X}_i$ $$\hat{s}_i = {_0}\hat{X}_i \hat{s}_i' \quad \text{Equation (19)}$$

Note the similarity between equations (17) and (18). For any particular state of the mechanism, equation (18) is a linear equation of the form $$\hat{a}_n = \Psi \hat{q} + \Psi_{const} \quad \text{Equation (20)}$$

where $\Psi$ is the reaction point Jacobian $$\Psi = [\hat{s}_1 \, \hat{s}_2 \, \ldots \, \hat{s}_n] \quad \text{Equation (21)}$$

and $$\Psi_{const} = \sum_{i=2}^{n} \left[ \sum_{j=1}^{i-1} \hat{s}_j \dot{q}_j \right] \times \hat{s}_i \dot{q}_i \quad \text{Equation (22)}$$

Thus, equation (20) provides the linear relation between joint and reaction point accelerations required for the controller architecture shown in FIG. 9. However, there is one additional complexity. The angular acceleration given as part of the spatial acceleration vector in equation (20) is an angular acceleration vector. This is suitable for situations where the desired angular velocity of the reaction point is specified using such a vector. Normally, however, this is not the case; desired angular acceleration is specified in terms of second derivatives of roll, pitch, and yaw angles (a.k.a. Euler angles). To convert to this form, consider first the angular velocity vector $\omega$. This is related to first derivatives of roll, pitch, and yaw by $$\omega = \begin{bmatrix} c_\alpha & -s_\alpha c_\gamma & 0 \\ s_\alpha & c_\alpha c_\gamma & 0 \\ 0 & s_\alpha & 1 \end{bmatrix} \begin{bmatrix} \dot{\gamma} \\ \dot{\beta} \\ \dot{\alpha} \end{bmatrix} \quad \text{Equation (23)}$$

where $\alpha$ is a rotation (of the reaction point) about the z (yaw) axis, $\beta$ is a rotation about the y (pitch) axis, and $\gamma$ is a rotation about the x (roll) axis. The rotation convention used is rotation of $\beta$ about the global (fixed) y axis, followed by rotation of $\gamma$ about the global x axis, followed by rotation of $\alpha$ about the global z axis. Using equation (23) and taking partial derivatives yields $$\dot{\omega} = \varphi + \begin{bmatrix} c_\alpha & -s_\alpha c_\gamma & 0 \\ s_\alpha & c_\alpha c_\gamma & 0 \\ 0 & s_\alpha & 1 \end{bmatrix} \begin{bmatrix} \ddot{\gamma} \\ \ddot{\beta} \\ \ddot{\alpha} \end{bmatrix} \quad \text{Equation (24)}$$

where $$\varphi \begin{bmatrix} (-s_\alpha \dot{\gamma} - c_\alpha c_\gamma \dot{\beta}) \dot{\alpha} + (s_\alpha s_\gamma \dot{\beta}) \dot{\gamma} \\ (c_\alpha \dot{\gamma} - s_\alpha c_\gamma \dot{\beta}) \dot{\alpha} + (-c_\alpha s_\gamma \dot{\beta}) \dot{\gamma} \\ (c_\gamma \dot{\beta}) \dot{\gamma} \end{bmatrix} \quad \text{Equation (25)}$$

Note that for a particular system state, equation (24) gives a linear relation between the angular acceleration vector, and the vector of second derivatives of Euler angles.

Equation (20) can be used to find the spatial acceleration of any reaction point. If we choose the CM of each link in the mechanism as a reaction point, then the acceleration of the system CM, in the x, y, and z directions, is given by $$\frac{d^2 CM}{dt^2} = \frac{1}{m_{tot}} \sum_{i=1}^{5} m_i \frac{d^2 CM}{dt^2} \quad \text{Equation (26)}$$

For the experiments described below, the following 12 values were chosen as the outputs to be controlled (the elements of $\gamma$ in FIG. 9): x and y CM position, body z position, body roll, pitch, and yaw angle, swing foot x, y, and z position, and swing foot roll, pitch, and yaw. These outputs were controlled using simple proportional-derivative (PD) control laws in $f_{cont}$, with feedback gains manually tuned.

Multivariable Optimal Controller

Using the linearization techniques described in the previous subsection, the system appears to be completely linearized and decoupled to the controller in FIG. 9, but $f_{cont}$ only if there are no constraints. Unfortunately, there are bounds on plant inputs due to saturation limits, and this complicates the problem. If the controller does not take these bounds into consideration, it could generate values to satisfy $\hat{y}_{des}$ that cause the bounds to be violated. For example, if the controller does not take into account the fact that the foot support polygon is of finite size, it might generate ankle torques that are too large, and that cause the foot to roll. The controller may be unable to satisfy the desired input while maintaining constraints. To avoid this type of infeasibility, slack variables are introduced for each element of $\hat{y}_{des}$, so that the new controller output is $$\hat{y}_{des} = \hat{y}_{cont\_out} + \hat{y}_{slack} \quad \text{Equation (27)}$$

This provides flexibility in that $\hat{y}_{des}$ conforms to the controller's linear PD control law (without regard to the actuation bounds), while $\hat{y}_{cont\_out}$, the true output of the controller, does obey actuation bounds. The goal of the overall control system is then to minimize $\hat{y}_{slack}$, taking into account the relative importance of each output. Thus, it is important to decide which outputs are the "important" ones, and therefore need to be controlled most closely. The goal for the overall control system is then to make the slack variables be 0 for the important outputs, and relatively small for the others.

The question now is how to formulate an optimization problem that minimizes the slack variables and obeys the actuation constraints. There are three types of constraints: 1) constraints on joint angle positions, 2) constraints on joint torques, and 3) constraints that keep the FRI within the support polygon. The FRI is the point on the foot/ground contact surface where the net ground reaction force would have to act to keep the foot stationary {4}. When in a single-support stance, if the FRI is outside the bounds of the actual support polygon, the support foot will begin to roll. Thus, keeping the FRI within these bounds amounts to limiting ankle torques of the stance leg so that the stance foot does not roll. The FRI is given by $$FRI_x = \frac{\sum_{i=1}^{5} m_i RPx_i (RP\ddot{z}_i + g) - \sum_{i=1}^{5} m_i RPz_i RP\ddot{x}_i - \sum_{i=1}^{5} H\dot{y}_i}{\sum_{i=1}^{5} m_i (RP\ddot{z}_i + g)} \quad \text{Equation (28)}$$

-continued $$FRI_y = \frac{\sum_{i=1}^{5} m_i RPy_i(RP\ddot{z}_i + g) - \sum_{i=1}^{5} m_i RPz_i RP\ddot{y}_i + \sum_{i=1}^{5} H\dot{x}_i}{\sum_{i=1}^{5} m_i(RP\ddot{z}_i + g)}$$

$$\dot{H}_{Gi} = I_{Gi}\dot{\omega}_i$$

where $\dot{\omega}_i$ is the angular acceleration vector of link i, in global coordinates.

Fortunately, all bounds can be expressed using linear inequality constraints. Since the equality constraints used for the linearization described in the previous section are all linear, it is possible to formulate the optimization problem as a quadratic program. The variables (columns) of this formulation are as follows: $\ddot{y}_{slack}$ (the slack variables), $\ddot{y}_{cont\_out}$ (the speci acceleration output by the controller to the linearized plant), $\ddot{q}_{des}$ (the joint accelerations), RP$\ddot{x}$, RP$\ddot{y}$, RP$\ddot{z}$ (the COM reaction point x, y, and z accelerations for each link), $\omega_x$ and $\omega_y$ components of angular acceleration of each link), and $\tau$ (the joint torques). Linear equality constraints of the quadratic programming formulation are as follows. Equation (27) relates $\ddot{y}_{slack}$ and $\ddot{y}_{cont\_out}$ through $\ddot{y}_{des}$, which is determined, outside the quadratic programming optimization, based on simple PD control laws that take y and $y_{des}$ as input. Equations (20) and (24) relate $\ddot{q}_{des}$ to $\ddot{y}_{cont\_out}$, and to RP$\ddot{x}$, RP$\ddot{y}$, RP$\ddot{z}$, $\omega_x$, $\omega$ Linear in-equality constraints of the formulation represent the bounds on joint angle positions, joint torques, and FRI. Bounds on FRI are represented using equation (28). Bounds on joint torques are represented simply as bounds on the $\tau$ variables in the quadratic program. Bounds on joint angle position are translated to bounds on joint angular accelerations which are set as bounds on the $\ddot{q}_{des}$ variables.

A quadratic cost function is used with costs assigned to the slack variables and also the joint torques. Slack costs for "important" outputs are higher than for the other outputs. In these experiments, the important outputs are CMx and CMy. These outputs also have correspondingly higher PD gains.

Sliding Control Framework

Feedback linearization is a powerful technique, but it can be insufficient for real plants because it assumes a perfect plant model. The sliding control algorithm {40} addresses this problem using a two-part structure. The first part is the nominal part; it assumes the model is perfect, and issues control commands using a feedback linearization based on this model. The second part contains additional corrective control terms that compensate for model inaccuracy.

The corrective control terms must be applied directly to the torques, the actual inputs to the plant. Thus, these terms bypass the kinematic and inverse dynamics models, and any associated inaccuracies in these models (see FIG. 9). The corrective terms are of the form $$-\lambda\dot{\tilde{q}} - ksgn(s) \qquad \text{Equation (29)}$$

where $\tilde{q}$ is the tracking error, $\lambda$ is the sliding mode constant, which controls convergence while on the sliding surface, s is the distance from the sliding surface, and k is made large enough to account for model uncertainty {40}.

Simulation Results

A series of tests was performed with initial conditions such that the ground projection of the CM was outside the support polygon, and all velocities were 0. For such initial conditions, the CM cannot be stabilized by stance ankle torques alone (without having the foot roll). A reference trajectory consisting of a single setpoint was input to the controller. This set-point specified desired position and velocity for CM and the other outputs.

FIG. 10 shows the system's recovery from a lateral initial displacement. FIG. 10(a) shows frame sequence, FIG. 10(b) shows lateral direction of CMP as dotted line and FRI as solid line; FIG. 10(c) shows desired CM acceleration as solid line, actual as heavy dashed line, and slack as dotted line, and FIG. 10(s) shows body roll angle, E. The side of the support polygon is at 0.05 m. As can be seen from FIG. 10b, the FRI remains within the support polygon, while the lateral CM position begins outside it, but is brought quickly to 0.

Figure 10A:
FIG. 10 illustrates Embodiment 2's recovery from a lateral initial displacement.
Figure 10B:
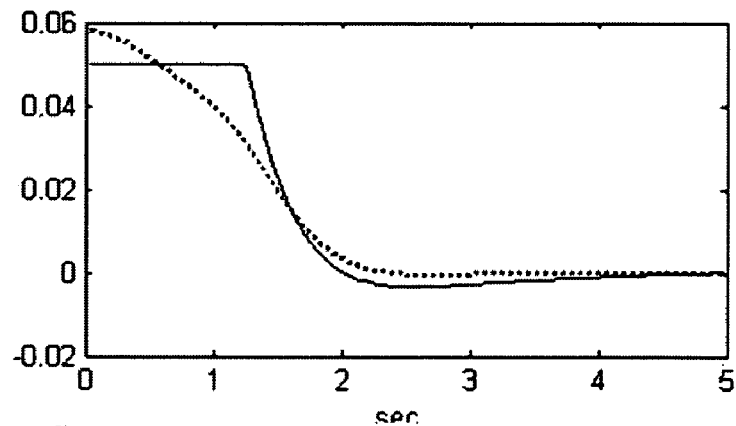
Figure 10C:
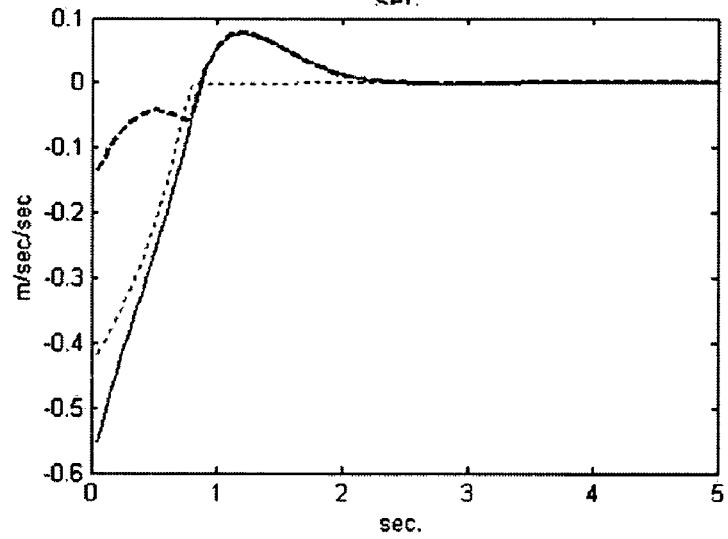
Figure 10D:
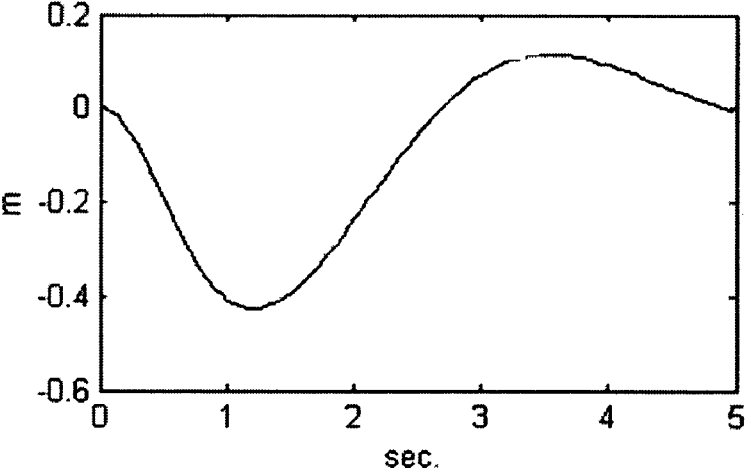
Figure 11A:
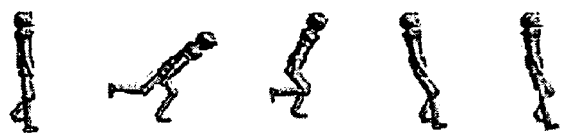
FIG. 11 shows the Embodiment 2's recovery from a forward initial displacement
Figure 11B:
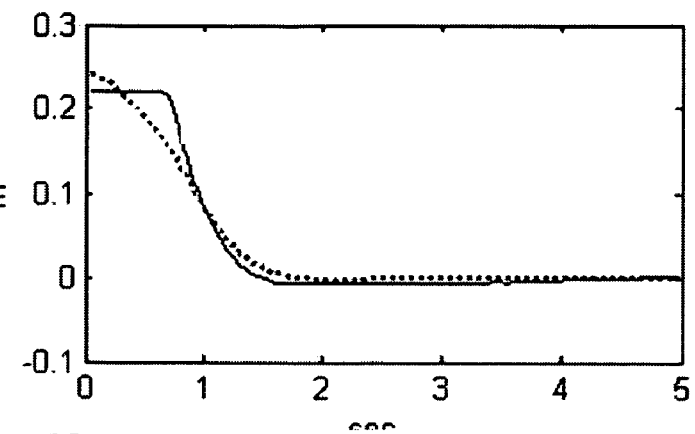
Figure 11C:
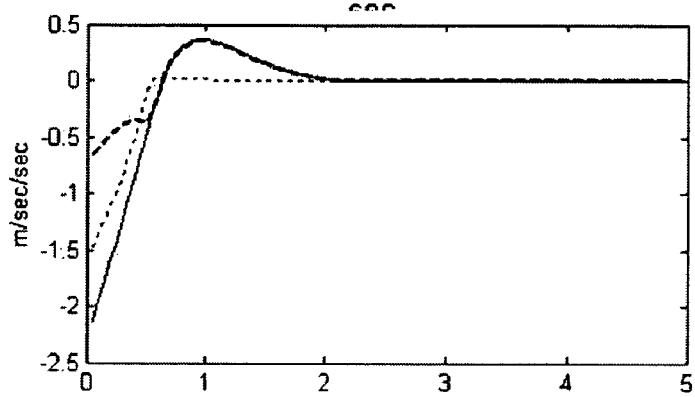
Figure 11D:
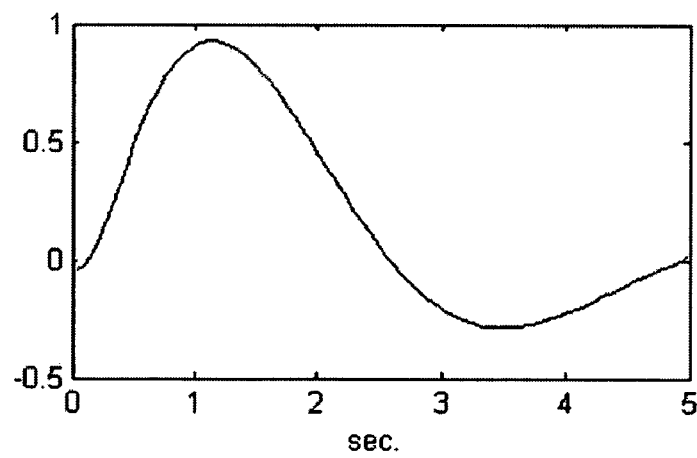

FIG. 10c shows desired, actual, and slack values for lateral CM acceleration. Note how the slack goes to 0 quickly, due to its high penalty. FIG. 10d shows the roll angle of the body. This converges, but more slowly than lateral CM position because it is less tightly controlled.

FIG. 11 shows the system's recovery from a forward initial displacement. FIG. 11(a) shows frame sequence, FIG. 11(b) shows forward direction CM as dotted line, FRI as solid line, FIG. 11(c) shows desired CM acceleration as solid line, actual as heavy dashed line, and slack as dotted line, FIG. 11(d) shows body pitch. The front of the support polygon is at 0.22 m. As can be seen from FIG. 11b, the FRI remains within the support polygon, while the forward CM position begins outside it, but is brought quickly to 0. FIG. 11c shows desired, actual, and slack values for forward CM acceleration. Note how the slack goes to 0 quickly, due to its high penalty. FIG. 11d shows the pitch angle of the body. This converges, but more slowly than forward CM position because it is less tightly controlled.

Figure 12A:
FIG. 12 shows the system's recovery from a combined forward and lateral displacement.
Figure 12B:
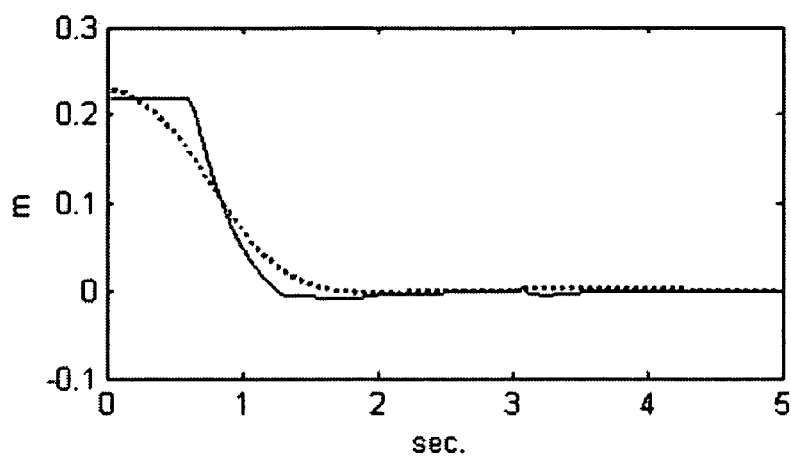
Figure 12C:
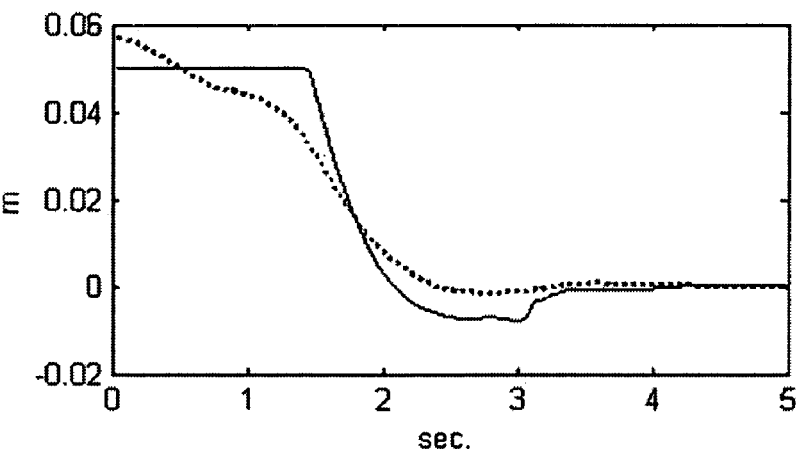

FIG. 12 shows the system's recovery from a combined forward and lateral displacement. FIG. 12(a) shows the frame sequence, FIG. 12(b) shows the forward direction CMP (as a dotted line), and FRI as solid line, and FIG. 12(c) shows lateral direction CMP and FRI.

Figure 13:
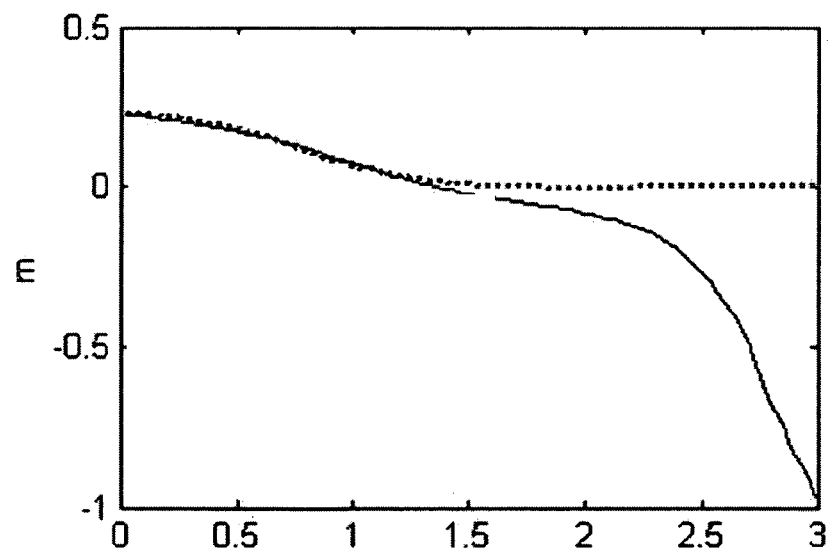
FIG. 13 compares the performance of Embodiment 2 with that of a simpler controller that uses a static Jacobian linearization

FIG. 13 compares the performance of this controller with that of a simpler controller that uses a static Jacobian linearization, showing the trajectory for forward CM using controller based on static Jacobian linearization (solid line), and using controller described here (dotted line). Initial conditions are the same as those in FIG. 12. As can be seen from FIG. 13, the static Jacobian controller has great difficulty with the initial conditions for the test in FIG. 12; the forward CM output becomes unstable, and the model falls down. The controller we have presented here handles these initial conditions easily.

Embodiment 2

Advantages and Improvements Over Existing Methods

The problem of taking into account dynamics has been addressed using a variety of approaches. A technique called "dynamic filtering" {43} involves adjusting an input set of joint trajectories so that dynamic balance constraints are satisfied. The input trajectories must be specified at a relatively high level of detail, and they have to be close to a correct solution. Slotine, {40}, developed a sliding controller with feedback linearization for control of robot manipulators. Kondak and Hommel, {44}, implemented a balance controller for simple mechanisms, using feedback linearization. However, due to the simplicity of the model, the issue of non-contact limb movement was not addressed. Also, control was in terms of joint state space rather than more abstract outputs of interest, thus making it difficult to prioritize multiple goals. Finally, model error was not taken into account.

An important feature of the controller is that the coordinated behavior of the stance leg and non-contact limbs is not controlled explicitly, but rather, emerges indirectly from a high-level specification of desired behavior. This specification is given in terms of set points and PD gains for the CM and other control outputs, in terms of constraints such as the one on the FRI, and in terms of penalties for slacks and torques in the optimization cost function.

An example of emerging behavior is in the case when the desired orbital angular momentum is greater than what can be provided by the stance ankle alone. Then, the deficit is made up by a non-zero spin angular momentum, which is created by movement of the non-contact limbs (the body and swing leg, in this case).

Another important feature of the controller is that, due to its extended range of operation, it can reject significant disturbances more easily than simpler controllers can. This also means that reference trajectories for the new controller need not be as detailed as those for simpler controllers. The reference trajectory for the tests of FIGS. 10-13 was a single set point for CM and the other outputs. Simpler controllers require more detailed reference trajectories, with more waypoints as a function of time. For example, the static Jacobian controller that failed in the test of FIG. 13 could be made to work for this case if a more detailed reference trajectories for stance leg, swing leg, and body were provided. However, this puts significant computational burden on the motion planning component of an integrated motion planning and control system. The motion planner has to be executed more frequently, when there are disturbances, and it must produce more detailed reference trajectories.

Embodiment 3

Motion Control Based on Angular Momentum, Effective Angle and Support Base Planning Here we describe a novel angular momentum-based, optimization control strategy {12} expressed in terms of global quantities, or quantities representing whole body translational and rotational dynamics. We introduce the Global Motion Control (GMC) framework suitable for the control of high level integrated quantities. Though the proposed optimization strategy and ZMP location may be expressed only in terms of global quantities, we extend our control framework from global state to joint space to effectively control balance as well as additional performance objectives. We next describe a soft-coded variant of a prioritized control architecture in which the priority list is decided in an automatic, time-local fashion. We also describe a non-prioritized approach for the control cases for which the cost function can be expressed in a particularly simple form such that an analytic solution is possible. We will further illustrate the later method by enforcing linear dynamics and truncating all control variables to linear terms in joint jerks. The description of Embodiment 3 concludes with a description of an approximate GMC-based time-local metric that may be utilized for support base planning during ground and flight locomotory phases.

GMC PD Control Law for Global State

Consider a simple PD control law relating whole body (that is, the body and any attached weight, such as a backpack) angular excursions, $\vec{\theta}$, spin angular momentum, $\vec{L}(\vec{r}_{CM})$, CM position, $\vec{r}_{CM}$, and CM momentum, $\vec{p}$, with desired whole body net moment about the CM, $\vec{\tau}_{des}$ ($\vec{r}_{CM}$), and net CM force, $\vec{F}_{des}$, or $$\vec{\tau}_{des}(\vec{r}_{CM}) = \dot{\vec{L}}_{tar}(\vec{r}_{CM}) - \tilde{a}\Delta\vec{\theta} - \tilde{b}\Delta\vec{L}(\vec{r}_{CM}) \quad \text{Equation (30a)}$$

$$\vec{F}_{des} = \dot{\vec{p}}_{tar} - \tilde{c}\Delta\vec{r}_{CM} - \tilde{d}\Delta\vec{p} \quad \text{Equation (30b)}$$

In (30a) $\Delta\vec{\theta} = \vec{\theta} - \vec{\theta}_{tar}$, $\vec{\theta}_{tar}$ is the target body angular $$\Delta\vec{L}(\vec{r}_{CM}) = \vec{L}(\vec{r}_{CM}) - \vec{L}_{tar}(\vec{r}_{CM}),$$

$\vec{L}_{tar}(\vec{r}_{CM})$ is the target spin angular momentum; and positive definite 3 by 3 matrices $\tilde{a}$ and $\tilde{b}$ are rotational stiffness and damping coefficients respectively. Analogously, in (30b) $\Delta\vec{r}_{CM} = \vec{r}_{CM} - \vec{r}_{CM\,tar}$, $\vec{r}_{CM\,tar}$ is the target CM position; $\Delta\vec{p} = \vec{p} - \vec{p}_{tar}$, $\vec{p}_{tar}$ is the target CM momentum; and positive definite 3 by 3 matrices $\tilde{c}$ and $\tilde{d}$ are stiffness and damping coefficients respectively. For practical purposes, instead of whole body angular excursions, which are not directly measurable quantities, one may consider using whole body principal angles defined by the relative orientations of the principal axes of the whole body inertia tensor with respect to the non-rotating lab frame axes.

The control designer may choose the diagonal form for matrices $\tilde{a}$, $\tilde{b}$, $\tilde{c}$ and $\tilde{d}$ and also set some of the diagonal elements to zero. For a humanoid robot in steady state walking, one may anticipate that the desired whole body angular excursion and the spin angular momentum would both be set to zero and the rotational stiffness and damping coefficients would then be adjusted to achieve a desired system response. Also, with $\vec{r}_{CM\,tar} = \vec{r}_{CM}(t=0) + \vec{p}_{tar} \cdot t/M$ $\vec{p}_{tar}$=const. for t∈(0,T) where T is chosen period of time.

The novelty of using the equations (30) is that it employs the rotational analog of the CM position and that it unifies all global quantities into one simple proportional derivative (PD) control law. We name this relationship the Global Motion Control (GMC) PD law. Similar to (30b), control of the CM position has been addressed by {45, 11} and joint linear and angular momentum control has been addressed by {31-32}.

The GMC PD law does not communicate a priori any type of stability metric. By definition it is only a tool for controlling the global state variables. However, if specific terms, like $\Delta\vec{L}(\vec{r}_{CM})|_{hor}$ with $\vec{L}_{tar}(\vec{r}_{CM})=0$, denote the stability metric, then equation (30) supplies important guidance for postural stability. Consider steady state walking: if rotational stiffness and damping coefficients ideally reflect the nature of the control problem then the actual moment, $\vec{\tau}_{act.}(\vec{r}_{CM})|_{hor.}$, of the opposite sign from $\vec{\tau}_{des.}(\vec{r}_{CM})|_{hor.}$ should be considered destabilizing. However even the stabilizing $\vec{\tau}_{act.}(\vec{r}_{CM})|_{hor.}$ may not guarantee actual postural stability unless it is the right magnitude.

We now generalize the angular momentum metric to include angular excursions as well. In addition we add some level of sensitivity to the external forcing and task dynamics.

Consider first the dynamics in the CM frame. In the non-inertial CM frame the body segments experience inertial forces in addition to external forcing. As we show next, CM non-inertiality embedded in (30b), i.e. $\vec{p}_{tar}\neq$const., may be coupled to rotational dynamics, (30a). The constant lab frame target acceleration may be thought to define a new effective gravity vector in the CM frame, FIG. 14a. The effect is identical to $$\dot{\vec{p}}_{tar}=0$$

when the plant experiences constant and uniform non-ground-reaction-forces (non-GRF) external forcing (e.g. wind), FIG. 14b. In direct analogy with regular upright posture, i.e. zero non-GRF external forcing and zero target acceleration, we propose that target angular excursion and momentum components orthogonal to the effective gravity vector should be set to zero. Therefore, (30a) may be now expressed in decoupled form as $$\vec{\tau}_{des.}(\vec{r}_{CM})=\dot{\vec{L}}(\vec{r}_{CM})-\tilde{a}_H\vec{\theta}\big|_{eff.hor.}-a_V\Delta\vec{\theta}\big|_{eff.ver.}-\tilde{b}_H\vec{L}(\vec{r}_{CM})\big|_{err.hor.}-b_V\Delta\vec{L}(\vec{r}_{CM})\big|_{eff.ver.}$$

Equation (31)

where the effective gravity vector is defined with $\vec{p}_{tar}$ and the slowly varying component of the non-GRF external forcing. The rotational stability measure is now represented by deviation of actual angular excursion and momentum from their most stable global state configuration $$\vec{\theta}_{tar}\big|_{eff.hor.}=0 \text{ and } \vec{L}_{tar}(\vec{r}_{CM})\big|_{eff.hor.}=0$$

Equation (32)

Figure 14:
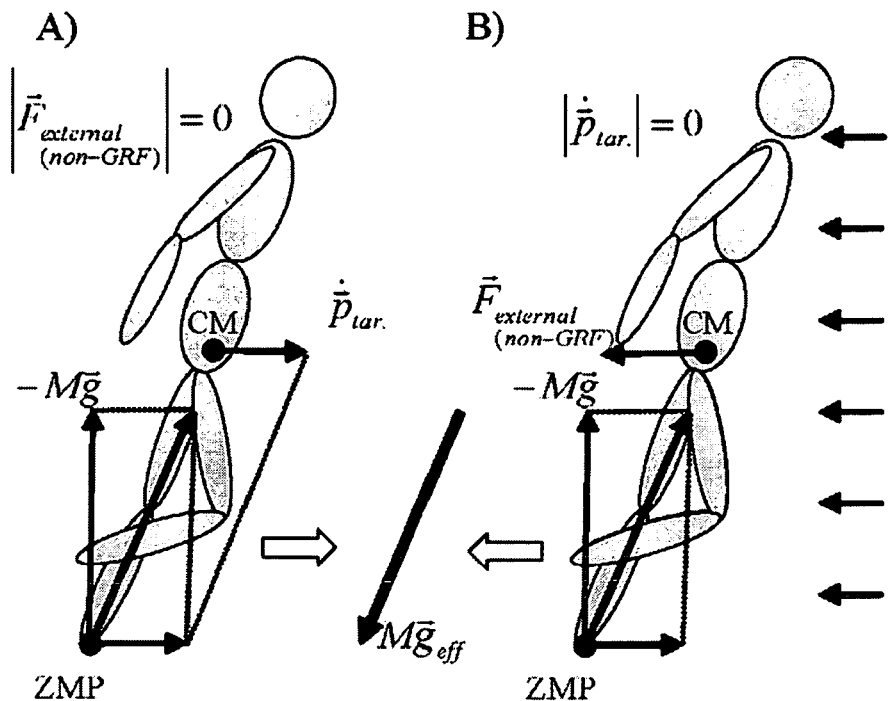
FIG. 14 illustrates the effective gravity vector for constant or slowly varying acceleration in Embodiment 3.

FIG. 14 illustrates the effective gravity vector for constant or slowly varying acceleration at the left in A) and non-GRF external forcing at the right in B).

Finally, all translational terms embedded in the GMC PD law, (30b), may be also thought of as indirect stability measures. However, they are more directly related to pure motion planning than to time-local postural stability measures. In other words, one is clearly more stable if the target CM trajectory doesn't require body collisions with walls or falling down over the edge of a cliff (or from a tight rope/balance beam).

From GMC PD Control Law to GMC Control Potential

Reference {31} utilized a version of (30) that included only damping elements. Numerical instabilities and hip angle limitations were encountered when all six elements of the target linear and angular momentum vector were specified. This observation motivated the introduction of a selection matrix that limited the number of elements to be controlled to only some of those six. This problem was further addressed with leg "constraints," i.e. by tuning the predefined desired velocity for each foot {31-32}. We find this problem to be quite general—not every global forcing ($\vec{F}$, $\vec{\tau}$) may be produced due to various physical limitations:

ZMP is confined within the support base,
limbs cannot penetrate other limbs or surrounding solid objects,
joint angles and joint actuations are limited,
ground friction coefficient is finite {46} etc.

If desired global forcing as suggested by (30) is outside the physically realizable region the simplest approach is to project the suggested solution to the physically realizable region. This approach was utilized in combination with prioritized control {8-10} for non-contact limb balancing {11}. A deficiency of the method is that with the ZMP at the boundary of the support base the smallest imprecision may destabilize the system. Yet another option is to use a method of control potentials.

The method of control potentials is particularly beneficial because a) physically meaningful solutions can be reinforced, as discussed below, and b) bias toward various target tasks can be easily introduced. The target task necessarily influences the choice of global forcing. For example, if the target task is to hold a glass of water, the whole body motion should not be very jerky.

We introduce the positive definite Global state control potential, that may be either defined on $V_{GS}(\vec{F},\vec{\tau})$ space with location of a minimum as suggested by the GMC PD law, (30), $$V_{GS}(\vec{\tau},\vec{F})=(\vec{\tau}-\vec{\tau}_{des.} \quad \vec{F}-\vec{F}_{des})\tilde{V}_{GS}\begin{pmatrix}\vec{\tau}-\vec{\tau}_{des}\\\vec{F}-\vec{F}_{des}\end{pmatrix},$$

Equation (33a)

or it may be defined directly on $\vec{\theta}$, $\vec{L}(\vec{r}_{CM})$, $\vec{r}_{CM}$, $\vec{p}$ space as a sum of quadratic terms centered about the target values, i.e.

$$V_{GSX}(\vec{X})=(\vec{X}-\vec{X}_{tar})\tilde{V}_{GSX}(\vec{X}-\vec{X}_{tar}),$$

$$V_{GS}=\sum_X V_{GSX}$$

Equation (33b)

Although control potential (33a) and (33b) may be equally applicable we will assume (33a) in the rest of the manuscript. The formulation (33a) is also more compatible with time local control approach that we enforce. For practical purpose one may assume diagonal $\tilde{V}_{GS}$ and introduce non-diagonal elements with two extra potentials described below.

Figure 15:
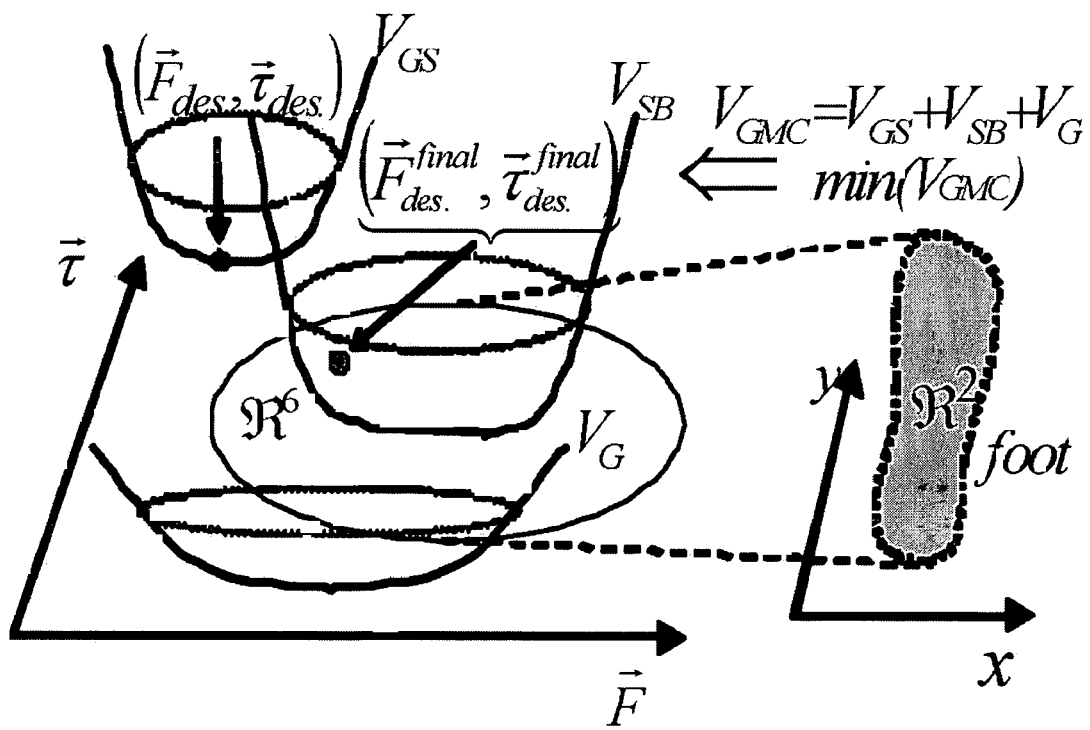
FIG. 15 illustrates the GMC potential represented as a sum of three control potentials.

Here we outline the basic structure of the GMC framework. As illustrated in FIG. 15, the GMC potential defined on the global forcing ($\vec{F},\vec{\tau}$) space may be represented as a sum of three control potentials:

Global State convex potential ($V_{GS}$), (33a), minimized at the desired force and torque as suggested by (30);

Support base potential ($V_{SB}$), enforcing ZMP within the support base and biased towards the innermost point (see next section);

Grand control potential ($V_G$), enforcing other physical limitations due to the plant properties, particular plant state and environment as well as introducing bias toward $V_G$ the target tasks. The represents a ($\vec{F}, \vec{\tau}$) projection of the Joint control potential ($V_j$) defined on joint space (see next section).

In FIG. 15, the GMC potential defined on ($\vec{F}, \vec{\tau}$) space is a sum of Global State ($V_{GS}$), Support Base ($V_{SE}$), and Grand ($V_G$) potentials. The final desired global forcing, $$\left( \vec{F}_{des}^{final}, \vec{\tau}_{des.}^{final} \right), is$$

then obtained by minimizing the unified GMC potential $$V_{GMC} = V_{GS} + V_{SB} + V_G \qquad \text{Equation (34)}$$

on ($\vec{F}, \vec{\tau}$) space. As discussed below, it may be beneficial to perform optimization directly on joint space instead of on smaller global forcing space.

GMC on Joint Angle Space

The performance of an on-line robotic controller depends on the physical model of the external world. Clearly, like a human, a robot has to tune the parameters of the physical model. However not all physical models are compatible with the tuning/adaptation schemes necessary for robotics applications. One example would be the model based on kinematical constraints. The kinematical constraints approach assumes an infinitely stiff ground and necessitates some of the GRF to be put by hand (only two contact points in 3-D may be resolved based on motion). In contrast, the viscous-elastic approach is more natural as it assumes that interaction between the end-effector and external world, represented by Lagrange function, may be modeled as a function of the relative position and speed. Dynamics of the system are completely specified with 6 root Euler-Lagrange (E-L) equations and $L_{joints}^N$ actuated joint angle E-L equations, or $$\frac{d}{dt}\left(\frac{\partial L}{\partial \dot{q}_{root}}\right) - \frac{\partial L}{\partial q_{root}} = \Gamma_{root} = 0 \qquad \text{Equation (35a)}$$

$$\frac{d}{dt}\left(\frac{\partial L}{\partial \dot{q}_{joints}}\right) - \frac{\partial L}{\partial q_{joints}} = \Gamma_{joints} \ne C \qquad \text{Equation (35b)}$$

This approach requires neither the position constraint equation nor the undetermined Lagrange multipliers required by the kinematical constraint approach. The interaction forces between body and external world are completely resolved by time local motion (i.e. state plus joint accelerations), i.e. they are not artificially assigned by the control designer. Finally, the characteristics of different surfaces can be modeled such that one can tell the difference between stepping on cement, deep snow, wet grass, or sandy beach.

Figure 16:
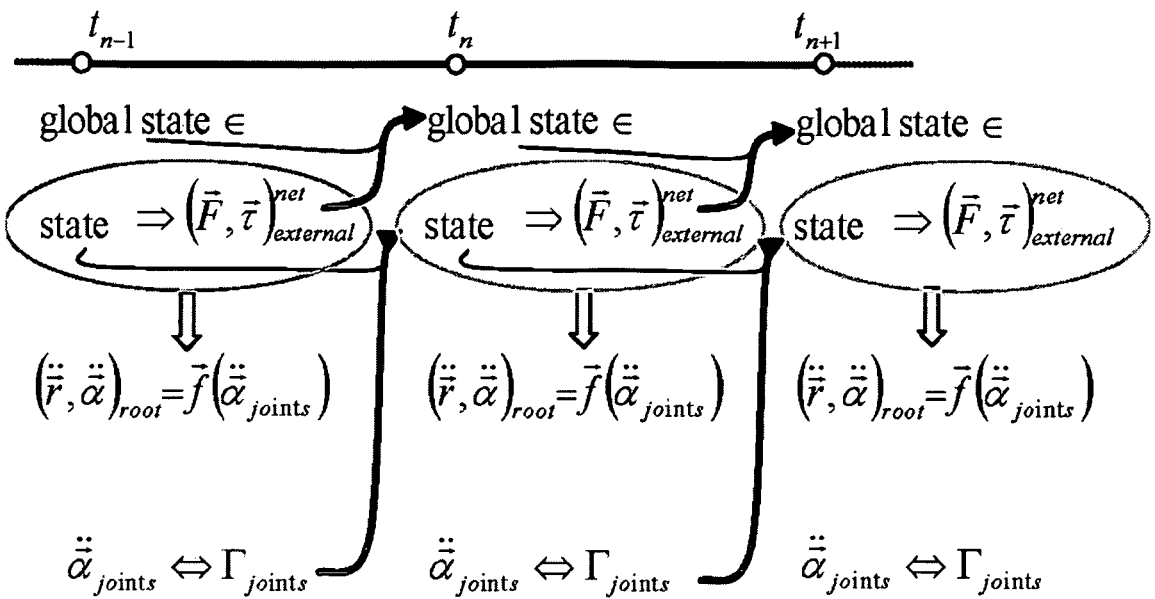
FIG. 16 is shows the flow of control in Embodiment 3.

As illustrated by FIG. 16 which shows the flow of control, the knowledge of state (positions and velocities) and accel erations at time $t_{n-1}$ defines the expectation of state at time $t_r$.

$$\dot{\alpha}_{expected}(t_n) \approx \dot{\alpha}(t_{n-1}) + \ddot{\alpha}(t_{n-1})(t_n - t_{n-1}) \qquad \text{Equation (36)}$$

$$\alpha_{expected}(t_n) \approx \alpha(t_{n-1}) + \dot{\alpha}(t_{n-1})(t_n - t_{n-1}) + \frac{1}{2}\ddot{\alpha}(t_{n-1})(t_n - t_{n-1})^2.$$

The state subsequently defines the expectation of forcing at time. Given the net force and net torque the root segment (usually body trunk) accelerations may be expressed in terms of state and joint accelerations, see (35a), all defined at time $t_n$. Joint accelerations subsequently define unique joint torques at time $t_n$, see (35b), and state at time $t_{n+1}$, similar to (36).

The control task is to choose, based on complete information of state plus accelerations at time, joint accelerations or equivalently joint torques at time in order to define state and forcing at time. The $i_{n-1}^t t_n t_{n+1}^{th}$ joint acceleration $\ddot{\alpha}_i(t_n)$ I may be represented as the sum of joint acceleration $\ddot{\alpha}_i(t_{n-1})$ and joint jerk $$\delta\ddot{\alpha}_i(t_n) = \ddot{\alpha}_i(t_n) - \ddot{\alpha}_i(t_{n-1}). \qquad \text{Equation (43)}$$

Hence, all quantities of interest at time may be represented as a function of $t_{n+1}\delta\ddot{\alpha}_i(t_n)$, i=1, . . . , $N_{joints}$ The expectation value of global kinematics quantities (CM position, CM momentum, whole body angular excursion and momentum about CM) at time $t_{n+1}$ is independent of $\delta\ddot{\alpha}_i(t_n)$. The expectation of position, velocity, forcing of any end-effector and therefore net force is a linear in $\delta\ddot{\alpha}_i(t_n)$. Finally the expectation of moment about CM and principal angles (see above) is a quadratic function in $\delta\ddot{\alpha}_i(t_n)$. The linear term, however, dominates for a small enough control time step (or small $\delta\ddot{\alpha}_i(t_n)$ as $\delta\ddot{\alpha}_i(t_n)_{\Delta t \to 0} \to 0$, $\forall i$). For small time step it makes sense to enforce linear dynamics for the optimizer by truncating higher order terms for all control variables.

The control problem may be even further simplified. Consider having only simple positive definite quadratic cost function terms $$V = \sum_j \left( k_j - \sum_i l_{ji}\delta\ddot{\alpha}_i \right)^2 \qquad \text{Equation (38)}$$

where j counts different cost function terms and i=1, . . . , $N_{joints}$. The minimum of V is expressed as a solution to a simple algebraic equation $$\vec{K} = \vec{L}\delta\vec{\alpha} \qquad \text{Equation (39)}$$

where and $$K_m = \sum_j k_j l_{jm} L_{mn} = \sum_j l_{jm} l_{jn}.$$

The otherwise very complex and computationally demanding optimization problem on joint jerk space is now stated as a single algebraic equation. Because the solution can be obtained extremely quickly the control time step can be made very small to substantiate linear approximation. In contrast to hard-coded (priority list defined in advance by the control designer) prioritized control {8-11} this method is analytical and non-prioritized.

Another avenue would be to use general cost function terms, i.e. not truncated to linear terms in joint jerks, and apply a method that we call soft-coded prioritized control. The controller, local in time, may first satisfy the most sensitive task, defined by having largest overlap with gradient of control potential in $\delta\alpha_r(t_n)$ space, and then continue with next sensitive task in leftover space etc. If the cost function indeed properly communicates the nature of the problem then the priority list should reflect that in time-local fashion.

The ZMP as a function of the CM position, net force ($\vec{F} = M\vec{\alpha}_{CM}$), and net moment about the CM can be expressed {23} as $$x_{ZMP} = x_{CM} - \frac{F_x}{F_z + Mg} z_{CM} - \frac{\tau_y(\vec{r}_{CM})}{F_z + Mg} \quad \text{Equation (40)}$$

$$y_{ZMP} = y_{CM} - \frac{F_y}{F_z + Mg} z_{CM} + \frac{\tau_x(\vec{r}_{CM})}{F_z + Mg}$$

We now introduce the positive definite Support base control potential, $V_{SB}$, defined on ($\vec{F}, \vec{\tau}$) space with the minimum corresponding to the innermost point of the support base ($x^*_{zmp}, y^*_{zmp}$), or $$V_{SB}(\vec{\tau},\vec{F}) = V_{SB}\left(x_{zmp}(\vec{\tau},\vec{F}), y_{zmp}(\vec{\tau},\vec{F})\right) = \quad \text{Equation (41)}$$

$$V_{sb1}\left((\vec{r}_{zmp} - \vec{r}^*_{zmp})\cdot\vec{n}_1\right)\cdot V_{sb2}\left((\vec{r}_{zmp} - \vec{r}^*_{zmp})\cdot\vec{n}_2\right),$$

where $V_{sb1}, V_{sb2}$ are positive definite functions (reinforcing ZMP inside the support base) and $\vec{n}_1 \perp \vec{n}_2$ are unit eigenvectors of the area matrix $$\vec{X}_{SB} = \quad \text{Equation (42)}$$

$$\int_{SB}\begin{bmatrix}(x - x^*_{zmp})^2 & (x - x^*_{zmp})(y - y^*_{zmp}) \\ (x - x^*_{zmp})(y - y^*_{zmp}) & (y - y^*_{zmp})^2\end{bmatrix} dxdy$$

and where integration is over the support base.

To summarize, the Support Base control potential, $V_{SB}$, penalizes net forcing when the ZMP is away from the innermost point. However, because this potential is only part of the GMC potential, the final choice of ZMP, while still physical, won't be at the innermost point of the support base.

The control designer may decide to include various terms in the Joint potential, $V_j$;

End-effectors position/velocity/forcing
Limits on joint angles
Sum of joint torques squared (static energy criteria)
Sum of joint powers (dynamic energy criteria) etc.

Although $V_j$ is originally defined on $\delta\ddot{\alpha}$ space it may be useful to project it down to smaller ($\vec{F}, \vec{\tau}$) space. In this way one obtains Grand potential $$V_G(\vec{F},\vec{\tau}) = \min V_j(\delta\ddot{\alpha})|_{(\vec{F},\vec{\tau})} \quad \text{Equation (43)}$$

as the minimum of $V_j$ subject to constraint. The motivation to study $V_o$ clearly comes from the idea that GMC optimization may be performed on small ($\vec{F}, \vec{\tau}$) space alone. However if there is a large mismatch in dimensions between joint $\delta\ddot{\alpha}$ space and ($\vec{F}, \vec{\tau}$) space then (43) may represent a difficult optimization problem. One would need to introduce a control simplification similar to the one described above. Then, however, the actual size of the space makes little difference and eventually all joint torques need be commanded.

To enforce no collisions between the end-effector and obstacle the control designer may use the attractive control potential term compatible with the analytical non-prioritized control approach. The attractive potential, however, should be such that the end-effector is attracted away from the obstacle. Still further, the magnitude of this term may be tuned to address the end-effector's speed.

GMC and Support Base Planning
Ground Phase Support Base Planning.

Here we describe a time-local control strategy for generation of the support base. This method is applicable when ground contact already exists and it is independent of other details (double vs. single support, left vs. right swing leg etc).

First we construct a virtual GMC potential, $$V_{GMC}^{virtual} = V_{GS} + V_{G(J)} \quad \text{Equation (44)}$$

Figure 17:
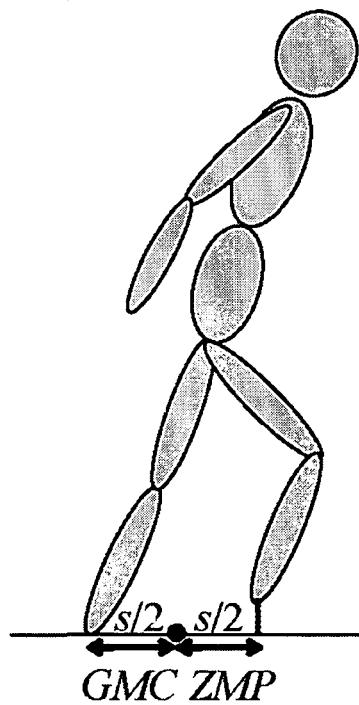
FIG. 17 illustrates GMC-based virtual ZMP during a) ground and b) flight phases.
Figure 17:
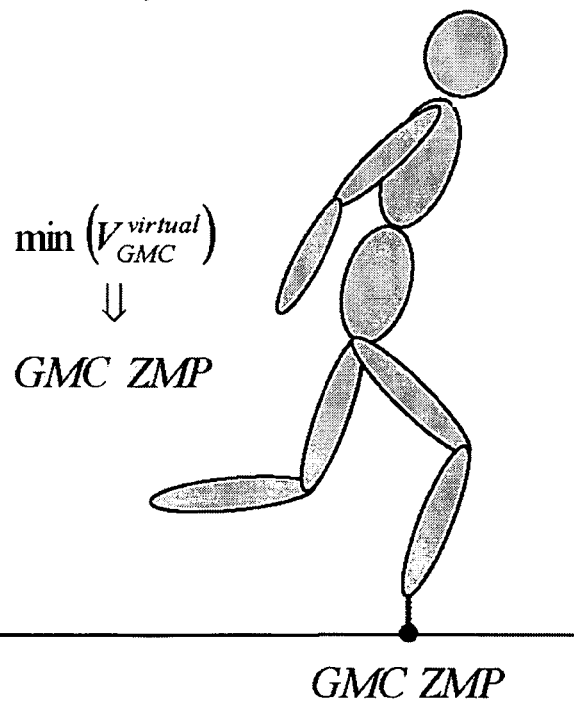

Next we find a minimum of virtual GMC potential and obtain ($\vec{F}_{des.}^{final}, \vec{\tau}_{des.}^{final})_{virtual}$. Using this virtual desired force and torque one may obtain a GMC-based virtual ZMP location on the ground. Now we enforce that the virtual ZMP should be located at the innermost point of the virtual support base defined by the convex hull obtained by the feet projection onto ground {7}, see FIG. 17a in FIG. 17 which illustrates GMC-based virtual ZMP during a) ground and b) flight phases. Therefore, indirectly, for the single support phase the virtual ZMP defines a target value for swing leg projection. For double support phase the virtual ZMP indirectly governs the feet rotation and toe-off.

Some simplification might be possible. For example, for some situations, one may neglect the Joint (or Grand) potential and use only Global State potential or the net forcing ($\vec{F}_{des.}, \vec{\tau}_{des.}$) defined by the GMC PD law, (30), to obtain a simplified virtual ZMP. This approach is different from the one proposed in {14} where the zero moment condition is enforced.

The actual timing of ground contact of the swing leg may be forced to coincide with the expected time of the ZMP entering the "dangerous zone" near the edge of the stance footprint. This expected time may be obtained from the measured ZMP position and velocity. Finally the swing leg velocity should be orthogonal to the surface at the moment of impact. The magnitude should be medium to avoid large stress.

Flight Phase Support Base Planning

The GMC is only indirectly applicable for the aerial phase. The system's dynamics are then characterized by only the force of gravity and zero moment about the CM and are independent of suggested net forcing. Therefore the CM follows a parabolic trajectory with zero horizontal acceleration and the whole body's angular momentum is a conserved quantity. Furthermore, the control potential is undefined on $V_{SB}(\vec{F},\vec{\tau})$ space without ground contact. However the control potential, defined on $V_{GS}(\vec{F},\vec{\tau})$ space, and $V_j\delta\ddot{\alpha}$ defined on $V_j\delta\ddot{\alpha}$ space, still exist. As we argued, the GMC may be applied indirectly. The aerial phase optimizer may choose the landing time, placement of the foot and body posture/joint torque distribution that facilitate the subsequent GMC performance on the ground.

In the aerial phase, $V_{GS}$ potential varies with time. Its minimum, defined by the GMC PD law, (30), may be used to define the desired position of the landing heel in the horizontal plane via (40), i.e $V_{GMC}^{virtual} \approx V_{GSvirtual}$. Alternatively, one may employ the minimum of $V_{GMC}^{virtual} = V_{GS} + V_j$. The tendency to reposition the landing heel as a response to change in linear/angular position, vertical linear momentum and other joint cost functions may be represented by $V_j$ potential with new cost function term. If landing time or position is given in advance, that should also be represented by appropriate weighting in $V_j$ potential.

Embodiment 4

Motion Control Based on CM Energetic and Zero Moment

Here we present a motion planner and controller based on two main premises:

Premise 1: Perfect exchange of CM kinetic energy of forward progression and CM potential energy or alternatively constancy of sum of these two energy terms.

Premise 2: Zero moment condition or alternatively CMP=ZMP.

Mathematically, these two conditions may be expressed as $$E_{kin.forward} + E_{potential} = \frac{mv_{forward}^2}{2} + mgz_{CM} = E_0 = const.$$ Equation (45)

where $$v_{forward} = \dot{x}_{CM}$$

(premise 1) and $$F_{G.R.X} = m\ddot{x}_{CM} = \frac{F_{G.R.Z}}{z_{CM}}(x_{CM} - x_{ZMP})$$ Equation (46)

where $F_G$ where $$F_{G.R.Z} = m(g + \ddot{z}_{CM})$$

(premise 2).

Now, one could solve for from equation (45) and obtain $z_{CM}$ $$z_{CM} = \frac{2E_0 - m\dot{x}_{CM}^2}{2mg}$$ Equation (47)

and differentiate twice with respect to time to obtain $$\ddot{z}_{CM} = -\frac{\dot{x}_{CM}^2 + \dot{x}\dddot{x}}{g}$$ Equation (48)

By combining equations (46-48) one obtain the third order differential equation $$m\ddot{x}_{CM} = \frac{m\left(g - \frac{\dot{x}_{CM}^2 + \dot{x}_{CM}\dddot{x}_{CM}}{g}\right)}{\frac{2E_0 - m\dot{x}_{CM}^2}{2mg}}(x_{CM} - x_{ZMP}) \Rightarrow$$ Equation (49)

$$\ddot{x}_{CM} = 2\frac{g^2 - \dot{x}_{CM}^2 - \dot{x}_{CM}\dddot{x}_{CM}}{(2E_0/m) - \dot{x}_{CM}^2}(x_{CM} - x_{ZMP}),$$

that can be solved by various standard methods for CMx trajectory $$x_{CM}(t) = f_x(x_{ZMP}(t), x_{CM}(0), \dot{x}_{CM}(0), \ddot{x}_{CM}(0), E_0)$$ Equation (51)

as function of the ZMPx trajectory, CMx initial conditions and constant $E_0$. This solution may be plugged back to equation (47) to gives related solution for CMz or $$z_{CM}(t) = f_x(x_{ZMP}(t), x_{CM}(0), \dot{x}_{CM}(0), \ddot{x}_{CM}(0), E_0)$$ Equation (51)

Given the CMx and CMz trajectories the control architecture of either one of three control embodiments described above (see description on Embodiment 1) may be used to generate joint angle trajectories. The proposed method may be then used in planning ZMPx trajectory such that target ZMPx trajectory leads to smallest variability in CM potential energy or this requirement can be combined (with appropriate weightings) with other requirements e.g. small impact forces.

Sensing and Control

Figure 18:
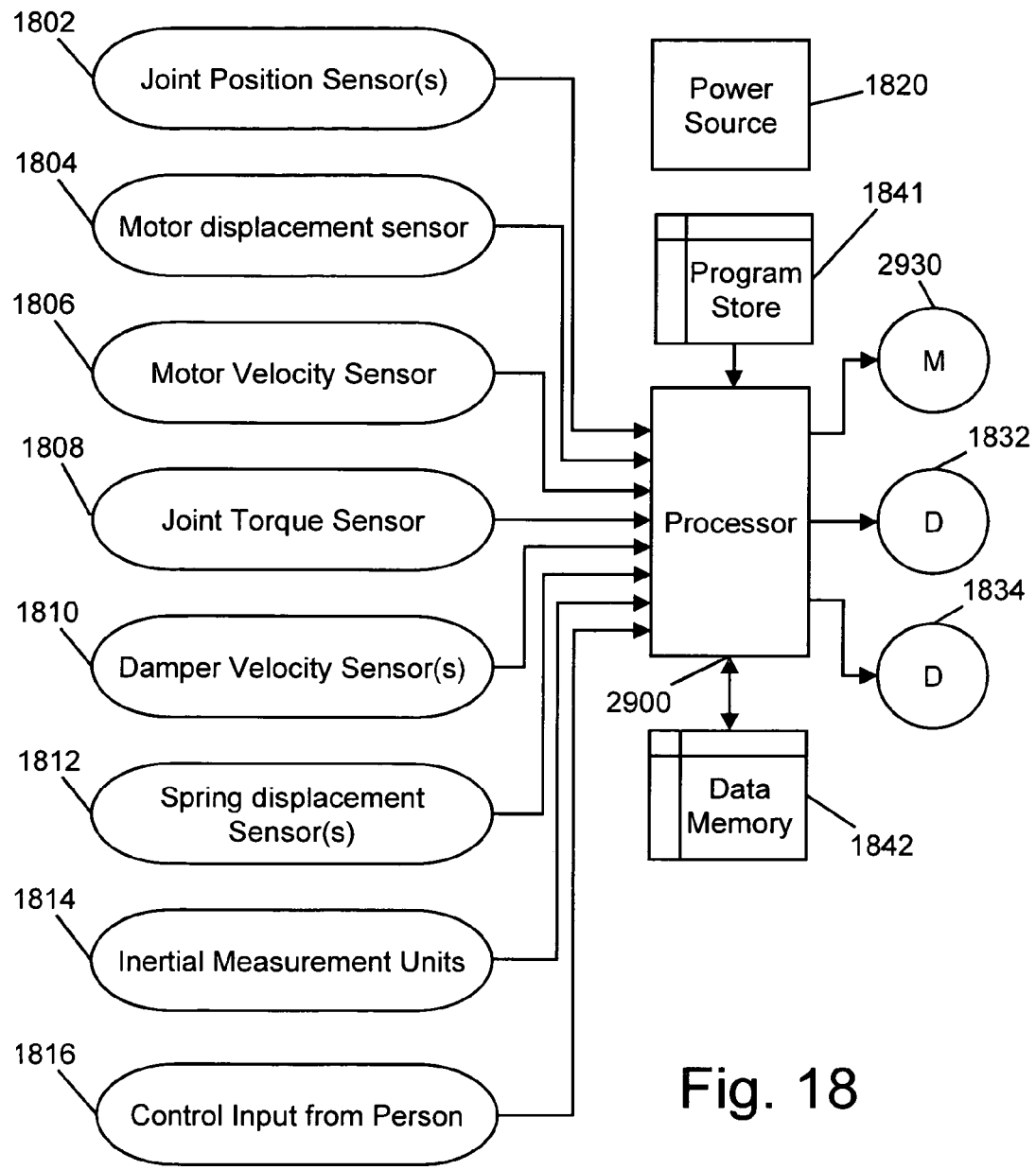
FIG. 18 depicts the general form of control system hardware employed to execute the control functions of Embodiments 1-4 and to utilize the results of these functions to control an artificial limb system.

As described in detail in U.S. patent application Ser. No. 11/395,448 filed on Mar. 31, 2006, the disclosure of which is incorporated herein by reference, the functions performed by the ankle, knee and hip joints during normal walking over level ground, and when ascending or descending a slope or stairs, may be performed in an artificial joint or limb using motors to act as torque actuators and to position the skeletal members during a specific times of walking cycle, using springs in combination with controllable dampers to act as linear springs and provide controllable damping at other times in the walking cycle. The specific mechanical structures, that is the combinations of motors, springs and controllable dampers used in the embodiments described in application Ser. No. 11/395,448, are specifically adapted to perform the functions needed by specific joint and limb structures. A variety of hardware controller mechanism may be employed to automatically control the motor and controllable dampers at the times needed, and any suitable control mechanism may be employed. FIG. 18 depicts the general form of a typical control mechanism in which a multiple sensors are employed to determine the dynamic status of the skeletal structure and the components of the hybrid actuator and deliver data indicative of that status to a processor seen at 1800 which produces control outputs to operate the motor actuator and to control the variable dampers.

The sensors used to enable general actuator operation and control can include:

(1) Position sensors seen at 1802 in FIG. 18 located at each biomimetic joint axis to measure joint angle (a rotary potentiometer), and at the motor rotor to measure total displacement of the motor's drive shaft (as indicated at 1804) and additionally the motor's velocity (as indicated at 1806). A single shaft encoder may be employed to sense instantaneous position, from which motor displacement and velocity may be calculated by the processor 1800.

(2) A force sensor (strain gauges) to measure the actual torque borne by the joint as indicated at 1808.

(3) Velocity sensors on each of the dampers (rotary encoders) as indicated at 1810 in order to get a true reading of damper velocity.

(4) A displacement sensor on each spring (motor series spring and global damper spring) as indicated at 1812 in order to measure the amount of energy stored.

(5) One or more Inertial Measurement Units (IMUs) seen at 1814 which can take the form of accelerometers positioned on skeletal members from which the processor 1800 can compute absolute orientations and displacements of the artificial joint system. For example, the IMU may sense the occurrence of events during the walking cycle such as heel strike and toe-off seen in FIGS. 1-3.

(6) One or more control inputs manipulatable by a person, such a wearer of a prosthetic joint or the operator of a robotic system, to control such things as walking speed, terrain changes, etc.

The values produced by the sensors and control inputs noted above together constitute data defining the current dynamic state of the appendage(s) being controlled. This current state information is processed by a closed-loop controller (implemented by the programmed processor 1800) such as a proportional-derivative (PD) or proportional-derivative-integral (PID) controller in which the current dynamic state data is compared with a desired state data to produce controls signals that are applied to controllable elements (e.g. motors and dampers) in the artificial appendage(s) (called the "plant"). For example, in the preferred Motion Control Embodiment 2, the controller which is depicted in FIG. 9, the linearized plant model produces data indicating desired joint angles, velocities and accelerations which can be compared with the measured joint angles, velocities and torque values from the sensors noted above to operate the motors and dampers which control the applied joint torques.

The processor 1800 preferably comprises a microprocessor which is carried on the body and typically operated from the same battery power source 1820 used to power the motor 1830 and the controllable dampers 1832 and 1834. A non-volatile program memory 1841 stores the executable programs that control the processing of the data from the sensors and input controls to produce the timed control signals which govern the operation of the actuator motor and the dampers. An additional data memory seen at 1842 may be used to supplement the available random access memory in the microprocessor 1800 and stores data such as the linear plant model data described in connection with FIG. 9.

Instead of directly measuring the deflection of the motor series springs as noted at (4) above, sensory information from the position sensors (1) can be employed. By subtracting the biomimetic joint angle from the motor output shaft angle, it is possible to calculate the amount of energy stored in the motor series spring. Also, the motor series spring displacement sensor can be used to measure the torque borne by the joint because joint torque can be calculated from the motor series output force.

REFERENCES

The following published materials provide background information relating to the invention. Individual items are cited above by using the reference numerals which appear below and in the citations in curley brackets.

{1} S. Schaal, "Is imitation learning the route to humanoid robots?" *Trends in Cognitive Sciences* 3:pp. 233-242, 1999.

{2} G. Pratt, "Legged Robots: What's New Since Raibert," *IEEE Robotics and Automation Magazine. Research Perspectives.* pp. 15-19, 2000.

{3} G. Pratt, "Low Impedance Walking Robots," *Integ. and Comp. Biol.* 42:pp. 174-181, 2002.

{4} A. Goswami, "Postural stability of biped robots and the foot-rotation indicator (FRI) point," *International Journal of Robotics Research* 18(6): pp. 523-533, 1999.

{5} D. Katic and M. Vukobratovic, "Survey of intelligent control techniques for humanoid robots," *Journal of Intelligent and Robotics Systems*, vol. 37, pp. 117-141, 2003.

{6} A. Goswami and V. Kallem, "Rate of change of angular momentum and balance maintenance of biped robots," *Proceedings of the IEEE International Conference on Robotics and Automation*, New Orleans, La., U.S.A., pp. 3785-3790, 2004.

{7} M. B. Popovic, A. Englehart and H. Herr, "Angular Momentum Primitives for Human Walking: Biomechanics and Control," *Proc. of the IEEE/RSJ International Conference on Intelligent Robots and Systems*, Sendai, Japan., pp. 1685-1691, 2004.

{8} O. Khatib, K. Yokoi, K. S. Chang, D. Ruspini, T. Holmberg and A. Casal, "Coordination and decentralized cooperation of multiple mobile manipulators," *Journal of Robotic Systems* 13(11):755-764, 1996.

{9} O. Khatib, L. Sentis, J. H. Park and J. Warren, "Whole body dynamic behavior and control of human-like robots," *International Journal of Humanoid Robotics*, 1(1): pp. 29-43, March 2004.

{10} L. Sentis and O. Khatib, "Task-Oriented Control of Humanoid Robots Through Prioritization," *IEEE-RAS/RSJ International Conference on Humanoid Robots*, Santa Monica, USA, November 2004.

{11} A. Hofmann, M. B. Popovic, S. Massaquoi and H. Herr, "A Sliding Controller for Bipedal Balancing Using Integrated Movement of Contact and Non-Contact Limbs," *Proceedings of the IEEE/RSJ International Conference on Intelligent Robots and Systems*, Sendai, Japan, pp. 1952-1959, 2004.

{12} Popovic, M. and Herr, H. 2005. Global Motion Control and Support Base Planning. *Proceedings of the IEEE/RSJ International Conference on Intelligent Robots and Systems*, Alberta, Canada.

{13} M. B. Popovic, W. Gu and H. Herr, "Conservation of Angular Momentum in Human Movement," *MIT AI Laboratory-Research Abstracts*, September 2002. pp. 231-232, 2002.

{14} M. B. Popovic, A. Hofmann and H. Herr, "Angular Momentum Regulation during human walking: Biomechanics and Control," *Proceedings of the IEEE International Conference on Robotics and Automation*, New Orleans, La., U.S.A., pp. 2405-2411, April 2004.

{15} H. Herr and M. B. Popovic, "Angular momentum regulation in human walking,". *J. Exp. Biol.* (Unpiblished), 2005.

{16} Hinrichs, R., Cavanagh, P. and Williams, K. (1983). Upper extremity contributions to angular momentum in running. *Biomechanics VIII-B*. Champaign, Ill.:Human Kinetics. pp. 641-647.

{17} Raibert, M. 1986. *Legged Robots that Balance*. The MIT Press, Cambridge Mass.

{18} Dapena, J. and McDonald, C. 1989. A three-dimensional analysis of angular momentum in the hammer throw. *Med. Sci. in Sports Exerc.* 21: 206-220.

{19} LeBlanc, M. and Dapena, J. 1996. Generation and transfer of angular momentum in the javelin throw. *In Proceedings of the 20th annual meeting of the American Society of Biomechanics*. Atlanta, Ga., pp.17-19.

{20} Gu, W. 2003. *The Regulation of Angular Momentum During Human Walking*. Undergraduate Thesis, Massachusetts Institute of Technology, Physics Department.

{21} Herr, H., Hofmann, A., Popovic, M. 2003. New Horizons for Orthotic & Prosthetic Technology: Merging Body and Machine. *Presented at the ZIF International Conference on Walking Machines*, Bielefeld, Germany.

{22} Hofmann, A. 2003. *Control Rules for Biomimetic Human Bipedal Locomotion Based on Biomechanical Principles*. Ph.D. Thesis Proposal, Submitted to the Computer Science and Electrical Engineering Department, Massachusetts Institute of Technology.

{23} M. B. Popovic, A. Goswami and H. Herr, "Ground Reference Points in Legged Locomotion: Definitions, Biological Trajectories and Control Implications," *International Journal of Robotics Research* (In press), 2005.

{24} Vukobratovic, M. and Juricic, D. 1969. Contributions to the synthesis of biped gait. *IEEE Transactions on Biomedical Engineering*, BME-16, pp. 1-6.

{25} Vukobratovic, M., Stepanenko, Y. U. 1973. Mathematical models of general anthropomorphic systems. *Mathematical Biosciences*. 17: 191-242.

{26} Li, Q., Takanishi, A. and Kato, I. 1993. Learning control for a biped walking robot with a trunk. *Proceedings of the IEEE/RSJ International Conference on Intelligent Robots and Systems*, Yokohama, Japan, pp. 1771-1777.

{27} Arakawa, T. and Fukuda, T. 1997. Natural motion generation of biped locomotion robot using hierarchical trajectory generation method consisting of GA, EP layers. *Proceedings of the IEEE International Conference on Robotics and Automation*, pp. 211-216.

{28} Huang, Q., Yokoi, K., Kajita, S., Kaneko, K., Aria, H., Koyachi, N. and Tanie, K. 2001. Planning walking patterns for a biped robot. *IEEE Transactions on Robotics and Automation*, vol. 17:(3)280-289.

{29} Popovic M., and Herr, H. 2003. Conservation of whole body angular momentum. *Presented at the Neuro-Muscular Research Center Seminar Series*. March 20, Boston University, Boston, Mass., USA.

{30} Popovic, M., Hofmann, A. and Herr, H. 2004b. Zero spin angular momentum control: definition and applicability. *Proceedings of the IEEE-RAS/RSJ International Conference on Humanoid Robots*, Los Angeles, Calif.

{31} Kajita, S., Kanehiro, F., Kaneko, K., Fujiwara, K., Harada, K., Yokoi, K. and Hirukawa, H. 2003. Resolved Momentum Control: Humanoid Motion Planning based on the Linear and Angular Momentum. *Proceedings of the IEEE/RSJ International Conference on Intelligent Robots and Systems*, Las Vegas, Nev., U.S.A., pp. 1644-1650.

{32} Kajita, S., Nagasaki, T., Kaneko, K., Yokoi, K. and Tanie, K. 2004. A Hop towards Running Humanoid Biped. *Proceedings of the IEEE International Conference on Robotics and Automation*, New Orleans, La., U.S.A., pp. 629-635.

{33} Simon F. Giszter, Ferdinando A. Mussa-Ivaldi, and Emilio Bizzi, "Convergent force fields organized in the frog's spinal cord," Journal of NeuroScience, 13(2): 467-491, 1993.

{34} K. A. Thoroughman and R. Shadmehr, "Learning of action through adaptive combination of motor primitives," Nature, 407:742-747, 2000.

{35} S. Schaal and C. G. Atkeson, "Constructive incremental learning from only local information," Neural Computation 10,8:2047-2084, 1998.

{36} T. D. Sanger, "Human arm movements described by a low-dimensional superposition of principal component," Journal of NeuroScience, 20(3):1066-1072, 2000.

{37} A. Fod, M. J. Mataric and O. C. Jenkins, "Automated Derivation of Primitives for Movements Classification," Autonomous Robots, 12(1):39-54, 2002.

{38} Tilley, A. R., and Dreyfuss, H., 1993 "The measure of man and woman," *Whitney Library of Design*, an imprint of Watson-Guptill Publications, New York.

{39} Winters, D. A. (1990) *"Biomechanics and Motor Control of Human Movement,"* John Wiley & Sons, Inc., New York.

{40} J. Slotine and W. Li, "Applied Nonlinear Control", Prentice Hall, New Jersey 1990.

{41} Paul, R. P., 1981a, "Robot Manipulators", Cambridge, Mass.: The MIT Press, pp. 9-64.

{42} Featherstone, R., 1987, "Robot Dynamic Algorithms", Boston, Mass., Kluwer Academic Publishers, pp. 155-172

{43} Kagami, S., Kanehiro, F., Tamiya, Y., Inaba, M., Inoue, H., 2001, "AutoBalancer: An Online Dynamic Balance Compensation Scheme for Humanoid Robots", in "Robotics: The Algorithmic Perspective", Donald, B. R., Lynch, K. M., and Rus, D., editors, A. K. Peters Ltd. pp. 329-340.

{44} Kondak, K. and Hommel, G. 2003. Control and online computation of stable movement for biped robots. *Proc. International Conference on Intelligent Robots and Systems (IROS)*. Las Vegas, Nev., USA.

{45} T. Sugihara, Y. Nakamura and H. Inoue, "Realtime Humanoid Motion Generation through ZMP Manipulation based on Inverted Pendulum Control," *Proceedings of the IEEE International Conference on Robotics and Automation*, pp. 1404-1409, 2002.

{46} S. Kajita, K. Kaneko, K. Harada, F. Kanehiro, K. Fujiwara and H. Hirukawa, "Biped walking on a low friction floor," *Proceedings of the IEEE/RSJ International Conference on Intelligent Robots and Systems*, Sendai, Japan., pp. 3546-3551, 2004.

CONCLUSION

It is to be understood that the methods and apparatus which have been described above are merely illustrative applications of the principles of the invention. Numerous modifications may be made by those skilled in the art without departing from the true spirit and scope of the invention.

What is claimed is:

1. A method for controlling the motion of a mechanism in an artificial appendage or a humanoid robot, said mechanism consisting of multiple articulated elements connected at one or more joints, said method comprising, in combination, the steps of:
   providing a controller for processing current state input data indicating the current dynamic state of said mechanism and desired state input data indicating the desired dynamic state of said mechanism to produce output element acceleration data indicating the amount by which said elements should be accelerated so that said current dynamic state is altered to more nearly conform to said desired dynamic state,
   employing a stored linear relationship between the element and joint accelerations of said mechanism to convert said output element acceleration data into computed joint acceleration data indicating the amount by which the movement of said elements about each of said joints should be accelerated,
   employing a stored linear relationship between joint accelerations and joint torques to compute joint torques that achieve desired joint accelerations.

2. A method for controlling the motion of a mechanism in an artificial appendage or a humanoid robot as set forth in claim 1 wherein said stored linear relationship relating joint accelerations and joint torques is a stored model of the inverse dynamics of said mechanism.

3. A method for controlling the motion of a mechanism in an artificial appendage or a humanoid robot as set forth in claim 1 wherein said stored linear relationship relating element accelerations and joint accelerations is a stored model of the inverse kinematics of said mechanism.

4. A method for controlling the motion of a mechanism in an artificial appendage or a humanoid robot as set forth in claim 1 wherein said controller further processes constraint data specifying permitted ranges of values for one or more parameters in a group of parameters consisting of output element accelerations, velocities, and positions; joint element accelerations, velocities, and positions; and joint torques.

5. A method for controlling the motion of a mechanism in an artificial appendage or a humanoid robot as set forth in claim 4 wherein said constraint data includes specified limits for the angular position for one or more of said joints.

6. A method for controlling the motion of a mechanism in an artificial appendage or a humanoid robot as set forth in claim 4 wherein said constraint data includes specified limits for the torque applied to one or more of said joints.

7. A method for controlling the motion of a mechanism in an artificial appendage or a humanoid robot as set forth in claim 4 wherein said constraint data includes the restriction that specified ones of said elements be positioned within predetermined regions relative to other elements.

8. A method for controlling the motion of a mechanism in an artificial appendage or a humanoid robot as set forth in claim 4 wherein said constraint data includes the restriction that the system's Zero Moment Point be within a restricted region.

9. A method for controlling the motion of a mechanism in an artificial appendage or a humanoid robot as set forth in claim 1 wherein said controller is a linear quadratic controller.

10. A method for controlling the motion of a mechanism in an artificial appendage or a humanoid robot as set forth in claim 1 wherein said output element acceleration data indicates the amount by which the center of mass of at least selected ones of said elements should be accelerated, and/or the amount by which the combined center of mass of one of, some of, or all of said elements should be accelerated.

11. A method for controlling the motion of a mechanism in an artificial appendage or a humanoid robot as set forth in claim 1 wherein said controller processes said current state input data and said desired state input data to control the center of mass position for said mechanism.

12. A method for controlling the motion of a mechanism in an artificial appendage or a humanoid robot as set forth in claim 11 wherein said controller further processes constraint data specifying permitted ranges of values for one or more parameters in a group of parameters consisting of output element accelerations, velocities, and positions; joint element accelerations, velocities, and positions; and joint torques.

13. A method for controlling the motion of a mechanism in an artificial appendage or a humanoid robot as set forth in claim 11 wherein said controller further processes said current state input data and said desired state input data to control the roll, pitch and yaw angle for the body supported by said mechanism.

14. A method for A method for controlling the motion of a mechanism in an artificial appendage or a humanoid robot as set forth in claim 11 wherein one of said articulated elements is a foot element that swings between contact positions on a support surface.

15. A method for controlling the motion of a mechanism in an artificial appendage or a humanoid robot as set forth in claim 14 wherein said controller further processes said current state input data and said desired state input data to control the roll, pitch and yaw angle of said foot element of said mechanism as it swings between contact positions on said support surface.

16. A method for controlling the motion of a mechanism in an artificial appendage or a humanoid robot as set forth in claim 11 wherein said controller further processes said current state input data and said desired state input data to control the angular momentum about the center of mass.

17. A method for controlling the motion of a mechanism in an artificial appendage or a humanoid robot as set forth in claim 11 wherein said controller prioritizes control goals, temporarily sacrificing lower priority goals in favor of higher priority goals.

18. A method for controlling the motion of a mechanism in an artificial appendage or a humanoid robot as set forth in claim 16 wherein said controller temporarily sacrifices goals of controlling angular momentum about the center of mass in favor of goals of controlling center of mass position.

19. A method for controlling the motion of a mechanism in an artificial appendage or a humanoid robot as set forth in claim 18 wherein said controller further processes constraint data specifying permitted ranges of values for one or more parameters in a group of parameters consisting of output element accelerations, velocities, and positions; joint element accelerations, velocities, and positions; and joint torques.

20. A method for controlling the motion of a mechanism in an artificial appendage or a humanoid robot as set forth in claim 1 wherein said controller processes said current state input data and said desired state input data in substeps comprising:
   producing control commands based on said computed joint torque data to control, the operation of said joints in said artificial appendage,
   producing tracking error data indicative of the difference between the current dynamic state of said artificial appendage as controlled by said control commands and said desired dynamic state, and delivering corrective commands based on said tracking error data directly to said joints to further modify said current dynamic state to compensate for errors in said stored linear relationship.

21. A method for controlling the motion of a mechanism in an artificial appendage or a humanoid robot as set forth in claim 20 wherein said controller incorporates a sliding control technique to compensate for said errors in said stored linear relationship.

* * * * *